United States Patent
Bradley et al.

(10) Patent No.: US 10,337,000 B2
(45) Date of Patent: Jul. 2, 2019

(54) EXPRESSION VECTOR PRODUCTION AND HIGH-THROUGHPUT CELL SCREENING

(71) Applicant: Kymab Limited, Cambridge (GB)

(72) Inventors: Allan Bradley, Cambridge (GB); E-Chiang Lee, Cambridge (GB); Qi Liang, Cambridge (GB); Hui Liu, Cambridge (GB); Andrew Wood, Cambridge (GB); Vivian Wong, Cambridge (GB)

(73) Assignee: KYMAB LIMITED, Cambridge (GB)

( * ) Notice: Subject to any disclaimer, the term of this patent is extended or adjusted under 35 U.S.C. 154(b) by 75 days.

(21) Appl. No.: 14/917,236

(22) PCT Filed: Sep. 18, 2014

(86) PCT No.: PCT/GB2014/052836
§ 371 (c)(1),
(2) Date: Mar. 7, 2016

(87) PCT Pub. No.: WO2015/040401
PCT Pub. Date: Mar. 26, 2015

(65) Prior Publication Data
US 2016/0208239 A1 Jul. 21, 2016

(30) Foreign Application Priority Data
Sep. 19, 2013 (GB) .................................. 1316644.2

(51) Int. Cl.
*C07K 16/00* (2006.01)
*C12N 15/10* (2006.01)
*C12N 15/85* (2006.01)

(52) U.S. Cl.
CPC .......... *C12N 15/1082* (2013.01); *C07K 16/00* (2013.01); *C12N 15/10* (2013.01); *C12N 15/1086* (2013.01); *C12N 15/1096* (2013.01); *C12N 15/85* (2013.01); *C07K 2317/14* (2013.01); *C07K 2317/52* (2013.01)

(58) Field of Classification Search
None
See application file for complete search history.

(56) References Cited

U.S. PATENT DOCUMENTS

| | | | |
|---|---|---|---|
| 6,116,099 A † | 9/2000 | Carl | |
| 6,258,529 B1 † | 7/2001 | Berdoz | |
| 6,919,183 B2 | 7/2005 | Fandl et al. | |
| 7,105,129 B2 † | 9/2006 | Ruddock | |
| 7,884,054 B2 † | 2/2011 | Shen | |
| 2002/0168702 A1 | 11/2002 | Fandl et al. | |
| 2007/0141048 A1 | 7/2007 | Oleksiewicz et al. | |
| 2007/0184546 A1 † | 8/2007 | Farrelly | |
| 2007/0280945 A1 | 12/2007 | Stevens et al. | |
| 2009/0081737 A1 † | 3/2009 | Brenner | |

FOREIGN PATENT DOCUMENTS

| | | |
|---|---|---|
| CN | 10299593 A | 9/2011 |
| WO | 2008142028 † | 5/2008 |
| WO | 2008/142028 A1 | 11/2008 |
| WO | 2010/109165 A2 | 9/2010 |
| WO | 2012/133572 A1 | 10/2012 |
| WO | 2013000982 A1 | 1/2013 |
| WO | 2013/188872 A1 | 12/2013 |
| WO | 2014/146074 A2 | 9/2014 |

OTHER PUBLICATIONS

Syed et al., "Next-generation sequencing library preparation: simultaneous fragmentation and tagging using in vitro transposition" 6(11) Nature Methods i-ii (2009).*
Beerli et al., "Isolation of human monoclonal antibodies by mammalian cell display." PNAS 105(38):14336-14341 (2008).
Franz et al., "Ex vivo characterization and isolation of rare memory B cells with antigen tetramers." Blood 118 (2):348-357 (2011).
Tiller et al., "Efficient generation of monoclonal antibodies from single human B cells by single cell RT-PCR and expression vector cloning." Journal of Immunological Methods 329(1):112-124 (2008).
Boria et al., "Primer sets for cloning the human repertoire of T cell Receptor Variable regions", BMC Immunol, 9:50 (2008).
Hogrefe et al., "Construction of phagemid display libraries with PCR-amplified immunoglobulin sequences", PCR Methods Appl, 4(2):S109-22 (1994).
Liao et al., "High-throughput isolation of immunoglobulin genes from single human B cells and expression as monoclonal antibodies", J Virol Methods, 158(1-2):171-9 (2009).
Dekosky et al., "High-throughput sequencing of the paired human immunoglobulin heavy and light chain repertoire", Nature Biotechnology, 31(2): 166-169 (2013).
Dekosky et al., "High-throughput sequencing of the paired human immunoglobulin heavy and light chain repertoire", Supplementary Information, Nature Biotechnology, 31(2): 166-169 (2013).
Duvall et al., "A novel platform to produce human monoclonal antibodies the next generation of therapeutic human monoclonal antibodies discovery", MABS, 3(2): 203-208 (2011).
Kurosawa et al., "Rapid production of antigen-specific monoclonal antibodies from a variety of animals", BMC Biology, 10 (2012).
Saridey et al., "PiggyBac Transposon-based Inducible Gene Expression in Vivo After Somatic Cell Gene Transfer", Molecular Therapy, 17(12): 2115-2120 (2009).
Smith et al., "Rapid generation of fully human monoclonal antibodies specific to a vaccinating antigen", Nature Protocol, 4(3): 372-384 (2009).
Tiller et al. "Single B cell antibody technologies" New Biotechnology 28(5):453-457 (2011).
Wang et al., "Human immunoglobulin variable region gene analysis by single cell RT-PCR." Journal of Immunological Methods 244(1-2):217-225 (2000).

(Continued)

*Primary Examiner* — Nancy J Leith
(74) *Attorney, Agent, or Firm* — Nixon Peabody LLP; David S. Resnick; Nicole D. Kling

(57) ABSTRACT

The present invention relates inter alia to expression vector production as well as application to the production of host cells for protein repertoire expression and high-throughput screening. The invention also relates to primers useful for PCR amplification of nucleotide sequences encoding human antibody variable domains.

16 Claims, 8 Drawing Sheets
Specification includes a Sequence Listing.

(56) References Cited

OTHER PUBLICATIONS

Publication relating to US20120178691—Printed from: https://www.lens.org/lens/patent/ (Jun. 15, 2018).

Hogrefe and Shapes. 1994. Construction of Phagemid Display Libraries with PCR-amplified Immunoglobulin Sequences. Genome Research. vol. 4, No. 2.†

Boria, et al. Aug. 2008. Primer Sets for Cloning the Human Repertoire of T Cell Receptor Variable Regions. BMC Immunology. vol. 9, No. 50.†

Liao, et al. Jun. 2009. High-Throughput Isolation of Immunoglobulin Genes from Single Human B Cells and Expression as Monoclonal Antibodies. J Virol Methods 158(1-2):171-9.†

Coronella, et al. Oct. 15, 2000. Amplification of IgG VH and VL (Fab) from Single Human Plasma Cells. Nucleic Acid Res. 28(20): e85.†

Weitkamp, et al. Apr. 2003. Generation of Recombinant Human Monoclonal Antibodies to Rotavirus from Single Antigen-Specific B Cells Selected with Fluorescent Virus-Like Particles. Journal of Immunological Methods. 275(1-2): 223-237.†

Jacobi, et al. Jun. 2008. Activated memory B cell subsets correlate with disease activity in systemic lupus erythematosus: delineation by expression of CD27, IgD, and CD95. Arthritis Rheum. 58(6): 1762-73.†

Bryskin and Matsumura. Jun. 2010. Overlap Extension PCR Cloning: A Simple and Reliable Way to Create Recombinant Plasmids. Biotechniques 48(6):463-5.†

\* cited by examiner
† cited by third party

According to Heavy Chain sequences

Based on single point neutralization assay

Dark circle/triangle = neutralisers

```
                        SEQUENCE LISTING

<160> NUMBER OF SEQ IDS NOS: 58

<210> SEQ ID NO 1
<211> LENGTH: 28
<212> TYPE: DNA
<213> ORGANISM: Homo sapiens
<220> FEATURE:
<223> OTHER INFORMATION: Human heavy chain variable region-specific
      sequence.

<400> SEQUENCE: 1
tctagagaaa accctgtgag cacagctc                                          28

<210> SEQ ID NO 2
<211> LENGTH: 24
<212> TYPE: DNA
<213> ORGANISM: Homo sapiens
<220> FEATURE:
<223> OTHER INFORMATION: Human heavy chain variable region-specific
      sequence.

<400> SEQUENCE: 2
gagaatcccc tgagagctcc gttc                                              24

<210> SEQ ID NO 3
<211> LENGTH: 24
<212> TYPE: DNA
<213> ORGANISM: Homo sapiens
<220> FEATURE:
<223> OTHER INFORMATION: Human heavy chain variable region-specific
      sequence.

<400> SEQUENCE: 3
tcagaagccc ccagagcaca acgc                                              24

<210> SEQ ID NO 4
<211> LENGTH: 26
<212> TYPE: DNA
<213> ORGANISM: Homo sapiens
<220> FEATURE:
<223> OTHER INFORMATION: Human heavy chain variable region-specific
      sequence.

<400> SEQUENCE: 4
tgggagaatc ccctagatca cagctc                                            26
```

```
<210> SEQ ID NO 5
<211> LENGTH: 24
<212> TYPE: DNA
<213> ORGANISM: Homo sapiens
<220> FEATURE:
<223> OTHER INFORMATION: Human heavy chain variable region-specific
      sequence.

<400> SEQUENCE: 5
acagaagccc ccagagcgca gcac                                          24

<210> SEQ ID NO 6
<211> LENGTH: 24
<212> TYPE: DNA
<213> ORGANISM: Homo sapiens
<220> FEATURE:
<223> OTHER INFORMATION: Human heavy chain variable region-specific
      sequence.

<400> SEQUENCE: 6
cccaccatgg acacactttg ctcc                                          24

<210> SEQ ID NO 7
<211> LENGTH: 25
<212> TYPE: DNA
<213> ORGANISM: Homo sapiens
<220> FEATURE:
<223> OTHER INFORMATION: Human heavy chain variable region-specific
      sequence.

<400> SEQUENCE: 7
tggactccaa ggcctttcca cttgg                                         25

<210> SEQ ID NO 8
<211> LENGTH: 29
<212> TYPE: DNA
<213> ORGANISM: Homo sapiens
<220> FEATURE:
<223> OTHER INFORMATION: Human heavy chain variable region-specific
      sequence.

<400> SEQUENCE: 8
tggacctcct gcacaagaac atgaaacac                                     29

<210> SEQ ID NO 9
<211> LENGTH: 27
<212> TYPE: DNA
<213> ORGANISM: Homo sapiens
<220> FEATURE:
<223> OTHER INFORMATION: Human heavy chain variable region-specific
      sequence.

<400> SEQUENCE: 9
gcagtcacca gagctccaga caatgtc                                       27

<210> SEQ ID NO 10
<211> LENGTH: 29
<212> TYPE: DNA
<213> ORGANISM: Homo sapiens
<220> FEATURE:
<223> OTHER INFORMATION: Human heavy chain variable region-specific
      sequence.

<400> SEQUENCE: 10
aagaagaagc ccctagacca cagctccac                                     29
```

```
<210> SEQ ID NO 11
<211> LENGTH: 26
<212> TYPE: DNA
<213> ORGANISM: Homo sapiens
<220> FEATURE:
<223> OTHER INFORMATION: Human heavy chain variable region-specific
      sequence.

<400> SEQUENCE: 11
tgagattccc aggtgtttcc attcag                                          26

<210> SEQ ID NO 12
<211> LENGTH: 28
<212> TYPE: DNA
<213> ORGANISM: Homo sapiens
<220> FEATURE:
<223> OTHER INFORMATION: Human heavy chain variable region-specific
      sequence.

<400> SEQUENCE: 12
agagccccag ccccagaatt cccaggag                                        28

<210> SEQ ID NO 13
<211> LENGTH: 25
<212> TYPE: DNA
<213> ORGANISM: Homo sapiens
<220> FEATURE:
<223> OTHER INFORMATION: Human heavy chain variable region-specific
      sequence.

<400> SEQUENCE: 13
ttcagtgatc aggactgaac acaca                                           25

<210> SEQ ID NO 14
<211> LENGTH: 29
<212> TYPE: DNA
<213> ORGANISM: Homo sapiens
<220> FEATURE:
<223> OTHER INFORMATION: Human heavy chain variable region-specific
      sequence.

<400> SEQUENCE: 14
ccccagcctt gggattccca agtgttttc                                       29

<210> SEQ ID NO 15
<211> LENGTH: 26
<212> TYPE: DNA
<213> ORGANISM: Homo sapiens
<220> FEATURE:
<223> OTHER INFORMATION: Human heavy chain variable region-specific
      sequence.

<400> SEQUENCE: 15
tgagattccc acgtgtttcc attcag                                          26

<210> SEQ ID NO 16
<211> LENGTH: 26
<212> TYPE: DNA
<213> ORGANISM: Homo sapiens
<220> FEATURE:
<223> OTHER INFORMATION: Human heavy chain variable region-specific
      sequence.

<400> SEQUENCE: 16
acttggtgat cagcacggag caccga                                          26
```

```
<210> SEQ ID NO 17
<211> LENGTH: 27
<212> TYPE: DNA
<213> ORGANISM: Homo sapiens
<220> FEATURE:
<223> OTHER INFORMATION: Human heavy chain variable region-specific
      sequence.

<400> SEQUENCE: 17
ctgggatttt caggtgtttt catttgg                                         27

<210> SEQ ID NO 18
<211> LENGTH: 26
<212> TYPE: DNA
<213> ORGANISM: Homo sapiens
<220> FEATURE:
<223> OTHER INFORMATION: Human kappa chain variable region-specific
      sequence.

<400> SEQUENCE: 18
ggagtcagac ccagtcagga cacagc                                          26

<210> SEQ ID NO 19
<211> LENGTH: 26
<212> TYPE: DNA
<213> ORGANISM: Homo sapiens
<220> FEATURE:
<223> OTHER INFORMATION: Human kappa chain variable region-specific
      sequence.

<400> SEQUENCE: 19
ggagtcagac ccactcagga cacagc                                          26

<210> SEQ ID NO 20
<211> LENGTH: 26
<212> TYPE: DNA
<213> ORGANISM: Homo sapiens
<220> FEATURE:
<223> OTHER INFORMATION: Human kappa chain variable region-specific
      sequence.

<400> SEQUENCE: 20
ggaatcagtc ccactcagga cacagc                                          26

<210> SEQ ID NO 21
<211> LENGTH: 26
<212> TYPE: DNA
<213> ORGANISM: Homo sapiens
<220> FEATURE:
<223> OTHER INFORMATION: Human kappa chain variable region-specific
      sequence.

<400> SEQUENCE: 21
ggagtcagtc tcagtcagga cacagc                                          26

<210> SEQ ID NO 22
<211> LENGTH: 28
<212> TYPE: DNA
<213> ORGANISM: Homo sapiens
<220> FEATURE:
<223> OTHER INFORMATION: Human kappa chain variable region-specific
      sequence.

<400> SEQUENCE: 22
atcaggactc ctcagttcac cttctcac                                        28
```

```
<210> SEQ ID NO 23
<211> LENGTH: 28
<212> TYPE: DNA
<213> ORGANISM: Homo sapiens
<220> FEATURE:
<223> OTHER INFORMATION: Human kappa chain variable region-specific
      sequence.

<400> SEQUENCE: 23
attaggactc ctcaggtcac cttctcac                                      28

<210> SEQ ID NO 24
<211> LENGTH: 26
<212> TYPE: DNA
<213> ORGANISM: Homo sapiens
<220> FEATURE:
<223> OTHER INFORMATION: Human kappa chain variable region-specific
      sequence.

<400> SEQUENCE: 24
gaggaactgc tcagttagga cccaga                                        26

<210> SEQ ID NO 25
<211> LENGTH: 25
<212> TYPE: DNA
<213> ORGANISM: Homo sapiens
<220> FEATURE:
<223> OTHER INFORMATION: Human kappa chain variable region-specific
      sequence.

<400> SEQUENCE: 25
gctacaacag gcaggcaggg gcagc                                         25

<210> SEQ ID NO 26
<211> LENGTH: 27
<212> TYPE: DNA
<213> ORGANISM: Homo sapiens
<220> FEATURE:
<223> OTHER INFORMATION: Human kappa chain variable region-specific
      sequence.

<400> SEQUENCE: 26
gactaccacc tgcaggtcag ggccaag                                       27

<210> SEQ ID NO 27
<211> LENGTH: 21
<212> TYPE: DNA
<213> ORGANISM: Homo sapiens
<220> FEATURE:
<223> OTHER INFORMATION: Human kappa chain variable region-specific
      sequence.

<400> SEQUENCE: 27
atggcctggt ctcctctcct c                                             21

<210> SEQ ID NO 28
<211> LENGTH: 21
<212> TYPE: DNA
<213> ORGANISM: Homo sapiens
<220> FEATURE:
<223> OTHER INFORMATION: Human kappa chain variable region-specific
      sequence.

<400> SEQUENCE: 28
atggccggct tccctctcct c                                             21
```

```
<210> SEQ ID NO 29
<211> LENGTH: 21
<212> TYPE: DNA
<213> ORGANISM: Homo sapiens
<220> FEATURE:
<223> OTHER INFORMATION: Human kappa chain variable region-specific
      sequence.

<400> SEQUENCE: 29
atgccctggg ctctgctcct c                                             21

<210> SEQ ID NO 30
<211> LENGTH: 21
<212> TYPE: DNA
<213> ORGANISM: Homo sapiens
<220> FEATURE:
<223> OTHER INFORMATION: Human kappa chain variable region-specific
      sequence.

<400> SEQUENCE: 30
atgccctggg tcatgctcct c                                             21

<210> SEQ ID NO 31
<211> LENGTH: 21
<212> TYPE: DNA
<213> ORGANISM: Homo sapiens
<220> FEATURE:
<223> OTHER INFORMATION: Human kappa chain variable region-specific
      sequence.

<400> SEQUENCE: 31
atggcctggg ctctgctgct c                                             21

<210> SEQ ID NO 32
<211> LENGTH: 21
<212> TYPE: DNA
<213> ORGANISM: Homo sapiens
<220> FEATURE:
<223> OTHER INFORMATION: Human kappa chain variable region-specific
      sequence.

<400> SEQUENCE: 32
atggcatgga tccctctctt c                                             21

<210> SEQ ID NO 33
<211> LENGTH: 21
<212> TYPE: DNA
<213> ORGANISM: Homo sapiens
<220> FEATURE:
<223> OTHER INFORMATION: Human kappa chain variable region-specific
      sequence.

<400> SEQUENCE: 33
atggcctgga ccctctcct g                                              21

<210> SEQ ID NO 34
<211> LENGTH: 21
<212> TYPE: DNA
<213> ORGANISM: Homo sapiens
<220> FEATURE:
<223> OTHER INFORMATION: Human kappa chain variable region-specific
      sequence.

<400> SEQUENCE: 34
atggcctgga ccctctcct c                                              21
```

```
<210> SEQ ID NO 35
<211> LENGTH: 21
<212> TYPE: DNA
<213> ORGANISM: Homo sapiens
<220> FEATURE:
<223> OTHER INFORMATION: Human kappa chain variable region-specific
      sequence.

<400> SEQUENCE: 35
atggcctgga cccctctctg g                                              21

<210> SEQ ID NO 36
<211> LENGTH: 21
<212> TYPE: DNA
<213> ORGANISM: Homo sapiens
<220> FEATURE:
<223> OTHER INFORMATION: Human kappa chain variable region-specific
      sequence.

<400> SEQUENCE: 36
atggcctgga ccgttctcct c                                              21

<210> SEQ ID NO 37
<211> LENGTH: 21
<212> TYPE: DNA
<213> ORGANISM: Homo sapiens
<220> FEATURE:
<223> OTHER INFORMATION: Human kappa chain variable region-specific
      sequence.

<400> SEQUENCE: 37
atggcatggg ccacactcct g                                              21

<210> SEQ ID NO 38
<211> LENGTH: 21
<212> TYPE: DNA
<213> ORGANISM: Homo sapiens
<220> FEATURE:
<223> OTHER INFORMATION: Human kappa chain variable region-specific
      sequence.

<400> SEQUENCE: 38
atggcctgga tccctctact t                                              21

<210> SEQ ID NO 39
<211> LENGTH: 21
<212> TYPE: DNA
<213> ORGANISM: Homo sapiens
<220> FEATURE:
<223> OTHER INFORMATION: Human kappa chain variable region-specific
      sequence.

<400> SEQUENCE: 39
atggcctgga tccctctcct g                                              21

<210> SEQ ID NO 40
<211> LENGTH: 21
<212> TYPE: DNA
<213> ORGANISM: Homo sapiens
<220> FEATURE:
<223> OTHER INFORMATION: Human kappa chain variable region-specific
      sequence.

<400> SEQUENCE: 40
atggcctgga ccgctctcct t                                              21
```

```
<210> SEQ ID NO 41
<211> LENGTH: 21
<212> TYPE: DNA
<213> ORGANISM: Homo sapiens
<220> FEATURE:
<223> OTHER INFORMATION: Human kappa chain variable region-specific
      sequence.

<400> SEQUENCE: 41
atggcctggg tctccttcta c                                              21

<210> SEQ ID NO 42
<211> LENGTH: 21
<212> TYPE: DNA
<213> ORGANISM: Homo sapiens
<220> FEATURE:
<223> OTHER INFORMATION: Human kappa chain variable region-specific
      sequence.

<400> SEQUENCE: 42
atggcctgga ccccactcct c                                              21

<210> SEQ ID NO 43
<211> LENGTH: 21
<212> TYPE: DNA
<213> ORGANISM: Homo sapiens
<220> FEATURE:
<223> OTHER INFORMATION: Human kappa chain variable region-specific
      sequence.

<400> SEQUENCE: 43
atggcttgga ccccactcct c                                              21

<210> SEQ ID NO 44
<211> LENGTH: 21
<212> TYPE: DNA
<213> ORGANISM: Homo sapiens
<220> FEATURE:
<223> OTHER INFORMATION: Human kappa chain variable region-specific
      sequence.

<400> SEQUENCE: 44
atggcctgga ctcctctcct c                                              21

<210> SEQ ID NO 45
<211> LENGTH: 21
<212> TYPE: DNA
<213> ORGANISM: Homo sapiens
<220> FEATURE:
<223> OTHER INFORMATION: Human kappa chain variable region-specific
      sequence.

<400> SEQUENCE: 45
atggcctgga ctcctctctt t                                              21

<210> SEQ ID NO 46
<211> LENGTH: 21
<212> TYPE: DNA
<213> ORGANISM: Homo sapiens
<220> FEATURE:
<223> OTHER INFORMATION: Human kappa chain variable region-specific
      sequence.

<400> SEQUENCE: 46
atggcctgga tgatgcttct c                                              21
```

<210> SEQ ID NO 47
<211> LENGTH: 21
<212> TYPE: DNA
<213> ORGANISM: Homo sapiens
<220> FEATURE:
<223> OTHER INFORMATION: Human kappa chain variable region-specific sequence.

<400> SEQUENCE: 47
atggcctggg ctcctctgct c                                              21

<210> SEQ ID NO 48
<211> LENGTH: 30
<212> TYPE: DNA
<213> ORGANISM: Homo sapiens
<220> FEATURE:
<223> OTHER INFORMATION: Human heavy chain constant region-specific sequence.

<400> SEQUENCE: 48
gctcttgcgg tagcccttga ccaggcatcc                                     30

<210> SEQ ID NO 49
<211> LENGTH: 25
<212> TYPE: DNA
<213> ORGANISM: Homo sapiens
<220> FEATURE:
<223> OTHER INFORMATION: Human heavy chain constant region-specific sequence.

<400> SEQUENCE: 49
cagatccagg ggccagtgga tagac                                          25

<210> SEQ ID NO 50
<211> LENGTH: 35
<212> TYPE: DNA
<213> ORGANISM: Homo sapiens
<220> FEATURE:
<223> OTHER INFORMATION: Human kappa chain constant region-specific sequence.

<400> SEQUENCE: 50
gtttctgatc gaactaacac tcattcctgt tgaag                               35

<210> SEQ ID NO 51
<211> LENGTH: 29
<212> TYPE: DNA
<213> ORGANISM: Homo sapiens
<220> FEATURE:
<223> OTHER INFORMATION: Human kappa chain constant region-specific sequence.

<400> SEQUENCE: 51
gacaatgggt gaagttgatg tcttgtgag                                      29

<210> SEQ ID NO 52
<211> LENGTH: 36
<212> TYPE: DNA
<213> ORGANISM: Homo sapiens
<220> FEATURE:
<223> OTHER INFORMATION: Human kappa chain constant region-specific sequence.

<400> SEQUENCE: 52
cgacaaccac tacctctatg aacattctgt aggggc                              36

<210> SEQ ID NO 53
<211> LENGTH: 25
<212> TYPE: DNA
<213> ORGANISM: Homo sapiens
<220> FEATURE:
<223> OTHER INFORMATION: Human kappa chain constant region-specific
      sequence.

<400> SEQUENCE: 53
cttctccacg gtgctcsctt catgc                                          25

<210> SEQ ID NO 54
<211> LENGTH: 35
<212> TYPE: DNA
<213> ORGANISM: Homo sapiens
<220> FEATURE:
<223> OTHER INFORMATION: CMV promoter sequence

<400> SEQUENCE: 54
cttactggct tatcgaaatt aatacgactc agatc                               35

<210> SEQ ID NO 55
<211> LENGTH: 313
<212> TYPE: DNA
<213> ORGANISM: Homo sapiens
<220> FEATURE:
<223> OTHER INFORMATION: piggyBac (PB) transposon inverted 5' terminal
      repeat element

<400> SEQUENCE: 55
gatatctata caagaaaat atatatataa taagttatca cgtaagtaga acatgaaata      60
acaatataat tatcgtatga gttaaatctt aaaagtcacg taaaagataa tcatgcgtca   120
ttttgactca cgcggtcgtt atagttcaaa atcagtgaca cttaccgcat tgacaagcac   180
gcctcacggg agctccaagc ggcgactgag atgtcctaaa tgcacagcga cggattcgcg   240
ctatttagaa agagagagca atatttcaag aatgcatgcg tcaattttac gcagactatc   300
tttctagggt taa                                                      313

<210> SEQ ID NO 56
<211> LENGTH: 235
<212> TYPE: DNA
<213> ORGANISM: Homo sapiens
<220> FEATURE:
<223> OTHER INFORMATION: piggyBac (PB) transposon inverted 3' terminal
      repeat element

<400> SEQUENCE: 56
tttgttactt tatagaagaa attttgagtt tttgtttttt tttaataaat aaataaacat     60
aaataaattg tttgttgaat ttattattag tatgtaagtg taaatataat aaaacttaat   120
atctattcaa attaataaat aaacctcgat atacagaccg ataaaacaca tgcgtcaatt   180
ttacgcatga ttatctttaa cgtacgtcac aatatgatta tctttctagg gttaa        235

<210> SEQ ID NO 57
<211> LENGTH: 594
<212> TYPE: PRT
<213> ORGANISM: Homo sapiens
<220> FEATURE:
<223> OTHER INFORMATION: Wildtype piggyBac transposase

```
<400> SEQUENCE: 57

Met Gly Cys Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
                20                  25                  30

His Val Ser Glu Asp Val Gln Ser Asp Thr Glu Glu Ala Phe Ile
            35                  40                  45

Asp Glu Val His Glu Val Gln Pro Thr Ser Ser Gly Ser Glu Ile Leu
        50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415
```

```
Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
        450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 58
<211> LENGTH: 594
<212> TYPE: PRT
<213> ORGANISM: Homo sapiens
<220> FEATURE:
<223> OTHER INFORMATION: Hyperactive piggyBac transposase

<400> SEQUENCE: 58

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Val Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Pro Thr Arg Arg Ser Arg Val Ser Ala Leu
            100                 105                 110

Asn Ile Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Ser Ala Thr Phe Arg Asp Thr Asn Glu Asp Glu Ile
                165                 170                 175
```

-continued

```
Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Val Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Gly Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Lys Glu Val Pro Gly Thr Ser
    530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Ser Ala Ser Cys Lys Lys
                565                 570                 575
```

```
Cys Lys Lys Val Ile Cys Arg Glu His Asn Ile Asp Met Cys Gln Ser
            580                 585                 590
Cys Phe
```

EXPRESSION VECTOR PRODUCTION AND HIGH-THROUGHPUT CELL SCREENING

CROSS-REFERENCE TO RELATED APPLICATIONS

This application is a 35 U.S.C. § 371 National Phase Entry Application of International Application No. PCT/GB2014/052836 filed Sep. 18, 2014, which designated the U.S., and which claims priority to GB Application No. 1316644.2 filed Sep. 19, 2013, the contents of each of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Jul. 16, 2015, is named K-00015-Sequence-listing-069496-086560.txt and is 22,643 bytes in size.

The present invention relates inter alia to expression vector production as well as application to the production of host cells for protein repertoire expression and high-throughput screening. The invention also relates to nucleic acids, PCR primers and mixtures useful for PCR amplification of nucleotide sequences encoding human antibody variable domains or homologous recombination with Ig loci in cells.

BACKGROUND

The art recognises the desirability of screening repertoires of cells or proteins to identify proteins of interest (POI) or cells expressing these. For example, the art comprises techniques to screen B-cells and repertoires of antibodies, in order to identify one or more cells that express antibodies displaying a desired characteristic (typically specific antigen binding). Screening is not confined to antibody screening, but also may be applicable to screening collections of other types of proteins for one or more desired characteristics.

In order to express protein repertoires, corresponding nucleotide sequences can be cloned into respective expression vectors and introduced (e.g., transfected) into host cells that can express the proteins. Commonly, molecular cloning is used to clone protein-encoding sequences from a repertoire into host cells. Molecular cloning has been applied to techniques of B-cell (lymphocyte) screening wherein B-cells are expanded by culturing, sorted into single cells (e.g., using a haemolytic plaque assay or fluorescent foci assay), antibody chain (or variable region) mRNA from the sorted cells is reverse transcribed and amplified using RT-PCR, amplified DNA undergoes molecular cloning to introduce antibody chain-encoding sequences into nucleic acid vectors and the vectors are then introduced into host cells for transient expression (where the vector is episomal) or for stable expression (by random integration into the host cell genome). See, for example, Proc Natl Acad Sci USA. 1996 Jul. 23; 93(15):7843-8, "A novel strategy for generating monoclonal antibodies from single, isolated lymphocytes producing antibodies of defined specificities", J S Babcook et al (known as the SLAM technique) and doi: 10.1016/j.jala.2009.05.004 Journal of Laboratory Automation October 2009 vol. 14 no. 5 303-307, "High-Throughput Screening for High Affinity Antibodies", S Tickle et al (known as the UCB SLAM technique).

Molecular cloning involves PCR amplifying cDNA (produced by RT-PCR of mRNA of POIs) with primers carrying restriction enzyme cloning sites. This produces PCR products in which each POI nucleotide sequence is flanked by restriction sites. The PCR products are then digested with the appropriate restriction enzymes and subcloned into empty expression vectors which provide a promoter and polyA signal by ligation as well as carry a selection marker. The ligated products are then transformed into E. coli and clones are selected by the presence of the marker. It is necessary to confirm and select clones with correct sequence insertions by laborious restriction mapping and sequencing of individual clones. Each single correct clone expression vector is then individually purified from E. coli and transfected into a host cell (e.g., a CHO or HEK293 mammalian cell) for transient or stable expression.

Molecular cloning is, therefore, a laborious technique involving multiple steps and is not well suited to high-throughput.

Transient expression, such as from a linear expression cassette, is usually limited and stable expression is preferred for longer-term expression. For stable expression, typically the POI-encoding sequence of interest is inserted into the mammalian genome by the classical integration method of spontaneous integration of foreign DNA (i.e., random integration in the genome). This approach often leads to significant transcriptional variation (and thus unpredictability and inconsistent POI expression) as a result of differences in the transgene copy number and the site of integration (see Henikoff S (1992), "Position effect and related phenomena", Curr Opin Genet Dev 2(6): 907-912; Martin D I, Whitelaw E (1996), "The variegating transgenes", Boessays 18(11): 919-923; and Whitelaw E et al. (2001), "Epigenetic effects on transgene expression", Methods Mol Biol. 158: 351-368). In addition, transgene fragments integrated in this way are often found to be inserted as concatemers which can result in gene inactivation by repeat-induced gene silencing (see Garrick D et al (1998), "Repeat-induced gene silencing in mammals", Nat Genet 18(1): 56-59; and McBurney M W et al (2002), "Evidence of repeat-induced gene silencing in cultured Mammalian cells: inactivation of tandem repeats of transfected genes", Exp Cell Res 274(1): 1-8). These problems hamper the production of repertoires of POIs and cell populations for expressing such POI repertoires.

Many technologies exist for the generation of monoclonal antibodies (mAbs) from human or transgenic animals carrying an antibody repertoire. Generally, mAbs are obtained from immortalization of B cells either by fusion (hybridoma technology) or transformation (virus transfection or oncogene transformation). These cell immortalization methods, however, are unsuitable for a comprehensive screening of large antibody repertoires, because they are highly biased, inefficient and typically only sample a minute proportion of the available repertoire (typically less than 0.1% (immortalised cells/input cells) of a B-cell repertoire obtained from an immunised mouse, for example). The use of alternative B-cell screening methods that do not require immortalisation, therefore, is attractive, but techniques currently face the problems discussed above.

SUMMARY OF THE INVENTION

The invention addresses the need for techniques of vector production that are amenable to high-throughput, reliable production suitable for repertoires and screening, particularly with the potential for automation.

Thus, a First Configuration of the Present Invention Provides:

In a first aspect,

A method of producing cells encoding a repertoire of proteins of interest (POI), the method comprising:

a) Providing a population of cells expressing a repertoire of POIs;

b) Sorting the population of cells to produce a sorted population of single cells, each cell comprising nucleic acid encoding a respective POI;

c) Amplifying the nucleic acid comprised by the sorted single cell population to produce a sorted repertoire of amplified nucleic acids encoding POIs;

d) Modifying sorted amplified POI-encoding nucleic acids from step (c) to produce a sorted repertoire of expression cassettes, each cassette comprising a nucleotide sequence encoding a POI and one or more regulatory elements for expressing the POI; and e) Transferring POI expression cassettes from said cassette repertoire to a sorted population of host cells while maintaining the POI expression cassette sorting and producing a sorted repertoire of host cells that expresses a sorted repertoire of POIs.

In an embodiment, sorting is maintained in step (e) by provision of the repertoires in a plurality of containers whose relative locations and overall arrangements are fixed. This enables high-throughput processing and automation of the method of the invention, e.g., for efficient and rapid cell screening to select one or more POI sequences of interest. Additionally or alternatively transfer of the expression cassettes in step (e) is carried out by batch transfer, and this too enables high-throughput processing and automation of the method of the invention.

In a second aspect,
An automated apparatus for performing the method of any preceding claim, the apparatus comprising
  a. Means for holding a sorted single cell population in a plurality of containers wherein each single cell is in a respective container, each cell comprising nucleic acid encoding a respective POI;
  b. Means for delivering PCR reagents to the containers for amplifying nucleic acid comprised by the sorted single cell population to produce a sorted repertoire of amplified nucleic acids encoding POIs;
  c. Means for delivering to the containers reagents for modifying sorted amplified POI-encoding nucleic acids to produce a sorted repertoire of expression cassettes, each cassette comprising a nucleotide sequence encoding a POI and one or more regulatory elements for expressing the POI;
  d. Means for holding a sorted population of host cells in a plurality of containers;
  e. Means for transferring POI expression cassettes from said cassette repertoire to the sorted population of host cells in the containers while maintaining the POI expression cassette sorting; and
  f. Means for carrying out transfection of expression cassettes into host cells in the containers to produce a sorted repertoire of host cells that expresses a sorted repertoire of POIs.

A Second Configuration of the Present Invention Provides:
In a first aspect,
An expression cassette for expression of a POI in a host cell, the cassette being provided by linear nucleic acid comprising a transposon, the transposon comprising 5'- and 3'-terminal transposon elements with a POI-encoding nucleotide sequence and regulatory element(s) for POI expression between the transposon elements.

In a second aspect,
A sorted population of expression cassettes encoding a repertoire of POIs corresponding to POIs expressed by a population of cells, each cassette comprising a nucleotide sequence encoding a member of the repertoire of POIs and one or more regulatory elements for POI expression, wherein each said cassette comprises the arrangement (in 5' to 3' direction): transposon element-[POI nucleotide sequence & regulatory element(s)]-transposon element, and expression cassettes for expression of POIs from different cells are isolated from each other in the sorted population (e.g., in different wells of a plate).

In a third aspect,
A method of making a transposon comprising a nucleotide sequence of interest (NOI), the method comprising
a. Providing a first nucleotide sequence comprising (in 5' to 3' direction) A, B and C, wherein A is a first homology sequence, B is a nucleotide sequence comprising the NOI and C is a second homology sequence;
b. Providing a first template nucleotide sequence comprising (in 5' to 3' direction) W and X, wherein W is a nucleotide sequence comprising a first transposon element and X is a third homology sequence; and
c. Providing a second template nucleotide sequence comprising (in 5' to 3' direction) Y and Z, wherein Y is a fourth homology sequence and Z is a nucleotide sequence comprising a second transposon element; and either
d. (i) Mixing the first nucleotide sequence with the first template to hybridise the first and third homology arms together and carrying out nucleic acid amplification and extension to extend the first nucleotide sequence using the first template to produce a first extended nucleotide sequence (first ENS) comprising (in 5' to 3' direction) W, B and C; and (ii) mixing the first ENS with the second template to hybridise the second and fourth homology arms together and carrying out nucleic acid amplification and extension to extend the first ENS to produce a second ENS comprising ((in 5' to 3' direction) W, B and Z; or
  (ii) Mixing the first nucleotide sequence with the second template to hybridise the second and fourth homology arms together and carrying out nucleic acid amplification and extension to extend the first nucleotide sequence using the second template to produce a third extended nucleotide sequence (third ENS) comprising (in 5' to 3' direction) A, B and Z; and
  (ii) mixing the third ENS with the first template to hybridise the first and third homology arms together and carrying out nucleic acid amplification and extension to extend the third ENS to produce a fourth ENS comprising ((in 5' to 3' direction) W, B and Z; or
  (iii) Mixing the first nucleotide sequence with the first and second templates to hybridise the first and third homology arms together and to hybridise the second and fourth homology arms together and carrying out nucleic acid amplification and extension to extend the first nucleotide sequence using the second template to produce a fifth ENS comprising ((in 5' to 3' direction) W, B and Z;
  and
e. Isolating an ENS comprising (in 5' to 3' direction) W, B and Z, thereby producing an isolated transposon comprising a NOI flanked by transposon elements; and
f. Optionally introducing the isolated transposon into a recipient cell so that the transposon integrates into the genome of the cell.

A Third Configuration of the Present Invention Provides:
A method of producing a host cell for expression of a POI, the method comprising
  a. Providing at least first and second expression cassettes, wherein each expression cassette comprises
    i. a first integration element and a second integration element 3' of the first integration element nucleotide sequence; and ii. between the integration elements a nucleotide sequence encoding a POI and one or more regulatory elements for expressing the POI;

iii. wherein the integration elements are capable of insertion into a nucleic acid by recognition of a predetermined nucleotide sequence motif of the nucleic acid using an integration enzyme;

b. Providing a host cell whose genome comprises a plurality of said motifs; and c. Simultaneously or sequentially introducing the first and second expression cassettes into the host cell, wherein each cassette is genomically-integrated in the host cell genome at a said motif for expression of POIs by the host cell; and d. Optionally producing a cell line expression POIs in a step comprising culturing the host cell.

A Fourth Configuration of the Present Invention Provides:

A nucleic acid mixture comprising a first isolated nucleic acid and a second isolated nucleic acid, wherein the first nucleic acid is capable of hybridising to a human antibody V region 5'UTR sequence of a gene comprised by a target nucleic acid, wherein the gene encodes a human V region; and the second nucleic acid is capable of hybridising to a second sequence, wherein the second sequence is comprised by the target nucleic acid and is 3' to the UTR sequence, wherein the first isolated nucleic acid comprises a sequence that is at least 90% identical to a sequence selected from the group consisting of SEQ ID NOs: 1-47.

A nucleic acid mixture comprising a first isolated nucleic acid and a second isolated nucleic acid, wherein the nucleic acids are different and selected from nucleic acids comprising a sequence that is at least 90% identical to a sequence selected from the group consisting of SEQ ID NOs: 1-47.

A method of amplifying a repertoire of human variable region sequences using one or more of the sequences.

DETAILED DESCRIPTION OF THE INVENTION

Figure 1A:
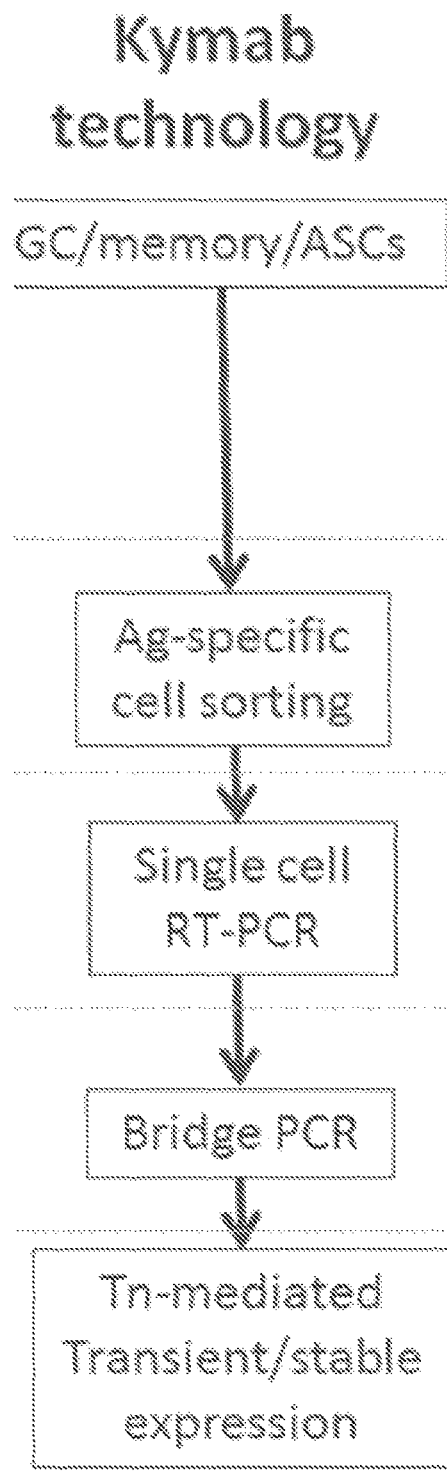
FIG. 1A is a schematic illustrating a non-limiting example of the method of the invention for producing a repertoire of antibody binding sites (POIs) in host cells (e.g., CHO or HEK293 cells).

FIG. 1 is a schematic illustrating an example of the method of the invention for producing a repertoire of antibody binding sites (POIs) in host cells (e.g., CHO or HEK293 cells), which is useful in a process of B-cell screening. The host cell repertoire produced at the end of the schematic in FIG. 1 is useful since the cells express antibody binding sites (e.g., $V_H/V_L$ pairs) that can be screened against a predetermined antigen to identify which cells express binding sites of interest. This thus enables genotype to phenotype linkage, allowing identification of nucleotide sequence that encodes a binding site of interest. This nucleotide sequence can then be used to construct cell lines for the stable production of desired antibody, e.g., to produce antibody pharmaceuticals or diagnostic or research reagents targeting the predetermined antigen. In an example, the host cell produced at the end of the schematic of FIG. 1 is itself a cell that stably expresses the binding site and this offers the possibility of convenient and efficient stable cell line generation for longer term manufacture of the binding site. As discussed further below, in an example site-mediated insertion of POI-encoding expression cassettes can be performed in host cells, which provides the added advantage of stable POI expression that avoids random integration and concatemers.

While examples are provided in terms of antibody binding sites, antibody variable domains and chains, the invention is not limited to such proteins. In this sense, the invention is applicable to any proteins of interest (POI). The term "protein" in this context also includes polypeptides and peptides which are of interest, as well as protein or polypeptide fragments or domains.

Turning to the non-limiting example of FIG. 1, in a first step, a desired B-cell population is provided, which may be germinal cells, memory cells, plasmablasts, plasma cells or generally may be antibody-secreting cells (ASCs), or mixtures of two or more of these B-cell types. The skilled person is familiar with selecting such populations, for example using cell surface markers optionally with FACS. Such markers may be selected from CD19, IgM, IgD, CD30 and CD95 for example, and may include a panel of one or more of these (eg. 1, 2, 3, 4), or may include a panel of all of these markers. Cells bearing these markers may be stained, for example, with any small molecule fluorophore which can be detected by the cell sorting system, such as Alexa-488, Alexa-647, Pacific Blue, R-phycoerythrin, fluorescein isothiocyanate, or allophycocyanin optionally conjugated to a cyanine dye, e.g. Cy7. The B-cell population may be generated in a preliminary step by isolation from one or more animals (e.g., mice, rats or humans or non-human animals), for example an animal that has been immunised with a target antigen. Thus, the method of the invention is useful for screening B-cell populations to identify one or more POI sequences derived from a B-cell wherein the POI binds the target antigen with a desired characteristic. Such a characteristic is, e.g., binding to the target antigen and/or a structurally-related, homologous or orthologous antigen (e.g., one from a different species); and/or binding an antigen with a desired affinity; and/or competition with a known antibody for binding a predetermined antigen (e.g., the target antigen); and/or binding a predetermined epitope.

Optionally, the desired input B-cell population (e.g., plasmablasts or plasma cells) can be selected by performing antigen-specific cell sorting using techniques known in the art (e.g., see Jin, A et al., Nature Medicine, 2009, 15(9): 1088-1093). The output is a population of B-cells that express antibody binding sites that specifically bind a predetermined target antigen. The inventors have found it advantageous to perform this step to streamline the overall B-cell screening process, thereby allowing for efficient and higher throughput screening.

Generally, antigen-specific GC (germinal centre) or memory B cells may be captured by labelled antigen because they dominantly express transmembrane antibodies on the cell surface. The antigen may be fluorescently labelled (for example, any small molecule fluorophore which can be detected by the cell sorting system, such as Alexa-488, Alexa-647, Pacific Blue, R-phycoerythrin, fluorescein isothiocyanate, or allophycocyanin optionally conjugated to a cyanine dye, e.g. Cy7). If the B cell population has been previously stained for initial selection, it is advantageous to use a fluorophore having a different emission wavelength to the fluorophore used in that initial selection, in order to facilitate the sorting process, e.g. using FACS. In an alternative, the cell may be simultaneously stained for presence of the cell selection marker and screened for binding to fluorescent antigen/antigen-bearing VLPs. Without being limited to theory, it is thought that, on the other hand, plasmablast or plasma cells would not be as easily captured by labelled antigen, because of their dominant expression of secreting antibody.

In an alternative embodiment, the antigen may be captured with virus-like particles (VLPs) with recombinant antigen on the surface. VLPs may be generated from CHO cells, KEK cells, mouse embryonic fibroblasts (MEFs) or other mammalian cell lines with co-expression of the recombinant antigen, the retrovirus gag protein, and MA-GFP (gag matrix fragment p15-GFP fusion protein). The gag protein expression enables VLP to bud from cells, and the MA-GFP labels the VLPs for fluorescence detection. Both gag and MA-GFP proteins are associated with the inner surface of the plasma membrane, and recombinant antigen is on the VLP surface. The antigens on the VLPs are presented in native form, directly expressed from recombinant cells without any step of purification or modification. The native form of an antigen should provide all the natural epitopes which greatly help selection of neutralizing antibodies. The high density of the antigen on the VLPs increases the signal/noise ratio for detection of cells expressing antigen-specific antibodies on the cell surface and greatly facilitates the sorting step. The recombinant VLPs can be generated with expression of different fluorescent proteins, such as MA-CFP or MA-YFP. Using multiplexing of VLPs with different antigen and different fluorescence protein, cells expressing high affinity binders, cross-reactive binders or homolog-specific binders can be selected. The cells expressing high affinity binders may be selected by cells with relative high affinity matrix (affinity matrix=the ratio of binding activity to low density antigen over to high density antigen VLPs). The cells expressing cross-reactive binders to orthologs or different antigens (for 2-in-1 bi-specific antibody isolation) can be selected by cells binding to different types of VLPs at the same time. The cells expressing homolog-specific binders also can be selected by cell only binding to specific antigen but not its homolog.

B-cells are thus sorted (e.g., using FACS) to provide a population of sorted, single B-cells. Typically, the B-cells are sorted into wells of a standard plate (e.g., a standard 96-well or 364-well plate) so that each single cell is in a respective well and not mixed with another cell. It is possible for there to be a minimal number (e.g., less than 5%, less than 3%, less than 2% or less than 1%, or non-detectable levels) of wells having no or more than one (e.g., two) cells, and this does not hamper the overall utility of the screening method (and is not considered part of the desired repertoire). Preferably, each well on the plate contains a single B-cell. Optionally, it is possible to culture cells directly before and/or after the cell sorting step, but the inventors have found this not be necessary unlike techniques in the art. Thus, by avoiding this step the method of the invention lends itself further to streamlining and high throughput.

Next, in the example shown in FIG. 1, POI-encoding nucleic acid is amplified. In the example, this is performed by reverse transcribing mRNA in cells of the sorted cell population (i.e., POI-encoding mRNA is converted to corresponding POI-encoding cDNA) and this is amplified using PCR. Standard RT-PCR can be used as will be familiar to the skilled person (e.g., see Dixon A K et al., Trends Pharmacol. Sci., 2000, 21(2): 65-70). This yields a repertoire of DNA encoding a repertoire of antibody variable regions. In this example, both $V_H$ and $V_L$ sequences are copied and amplified for each sorted cell. The skilled person will know that each cell expresses a single type of antibody binding site, thus only a single type of amplified $V_H$ sequence and a single type of $V_L$ sequence will be amplified per single sorted cell (thus, where wells are used, only a single $V_H$ and $V_L$ type per well be obtained, which thereby retains the grouping of $V_H$ and $V_L$ sequences forming binding sites).

POI-encoding sequences are also modified to produce a repertoire of expression cassettes for expressing POIs from host cells in a later stage of the method. The expression cassettes contain a POI-encoding nucleotide sequence and one or more regulatory elements for expression (e.g., a promoter and/or an enhancer and/or a polyA). In an embodiment, the amplification and modification steps can be performed simultaneously using PCR and appropriate templates and primers as will be apparent to the skilled person. In another embodiment, amplification and modification are carried out in separate steps, e.g., amplification and then modification. In the example of FIG. 1, RT-PCR is first carried out and then the amplified POI-encoding sequences are modified to produce expression cassettes each comprising (in 5' to 3' direction): promoter-POI nucleotide sequence-polyA. In this example, flanking transposon elements are also added. The transposon elements can be piggyBac (PB) transposon inverted terminal repeat elements to form a transposon nucleic acid comprising the structure: [5' PB element]-[promoter]-[POI nucleotide sequence]-[polyA]-[3' PB element]. In an example, each expression cassette is provided by linear DNA comprising or consisting of the transposon.

PB 5'element (SEQ ID NO: 55):

```
GATATCTATAACAAGAAAATATATATATAATAAGTTATCACGTAAGT

AGAACATGAAATAACAATATAATTATCGTATGAGTTAAATCTTAAAA

GTCACGTAAAAGATAATCATGCGTCATTTTGACTCACGCGGTCGTTA

TAGTTCAAAATCAGTGACACTTACCGCATTGACAAGCACGCCTCACG

GGAGCTCCAAGCGGCGACTGAGATGTCCTAAATGCACAGCGACGGAT

TCGCGCTATTTAGAAAGAGAGAGCAATATTTCAAGAATGCATGCGTC

AATTTTACGCAGACTATCTTTCTAGGGTTAA
```

PB 3'element (SEQ ID NO: 56):

```
TTTGTTACTTTATAGAAGAAATTTTGAGTTTTTGTTTTTTTTAATA

AATAAATAAACATAAATAAATTGTTTGTTGAATTTATTATTAGTATG

TAAGTGTAAATATAATAAAACTTAATATCTATTCAAATTAATAAATA

AACCTCGATATACAGACCGATAAAACACATGCGTCAATTTTACGCAT

GATTATCTTTAACGTACGTCACAATATGATTATCTTTCTAGGGTTAA
```

As shown in the example of FIG. 1, bridge PCR (see, e.g., Mehta R. K., Sihgh J., Biotechniques, 1999, 26(6):1082-1086) can be used to construct the transposon by adding the flanking transposon elements.

At this stage of the method, one has obtained a repertoire of expression cassettes encoding a repertoire of POI-encoding nucleotide sequences derived from the input population of cells. In this example, the amplification and modification procedures are carried out on the single cells that are sorted in wells on one or more plates. Thus, the result is a sorted repertoire of expression cassettes (in this case one per single well, the well contains a plurality of one type of $V_H$ expression cassette and one type of $V_L$ expression cassette derived from one type of antibody binding site of a single input cell). Next, the sorted expression cassettes (in the present example, contained in respective transposons and optionally as linear DNAs) are transferred to host cells to produce a sorted repertoire of host cells that expresses a sorted repertoire of POIs. This can be performed, in the present example, by transferring expression cassettes from wells on one plate (or one set of plates) to one or more other plates having a plurality of cells containing host cells (e.g., identical types of cells of the same cell line, e.g., CHO or HEK293 or yeast cells). In this embodiment, the sorted cassette repertoire can be transferred manually or with a robot using a multi-channel pipette (e.g., a 4, 8, 12, 16 (2×8), 64 (8×8), 96 (12×8), 384 or 1536 channel pipette as is known in the art) to simultaneously retrieve cassettes (in this case sorted VH/VL pairs of cassettes) from individual wells on a first plate and transfer to corresponding wells on a second plate, wherein those wells contain host cells. By doing this, the relative location and sorted nature of the expression cassettes is maintained when transferring to host cells. This has the advantage of maintaining linkage of $V_H/V_L$ cassette sequence pairs without mixing (i.e., per well on the second plate, the well contains host cells and $V_H$ and $V_L$ sequences derived from a single input B-cell only). Advantageously, also if some cassette sample is left on the first plate, one can then easily identify one or more wells as a source of useful POI-encoding sequence (and expression cassette and transposon) by reference to desired positives found on the second plate following screening of the second plate for a desired antibody binding site characteristic. Also, advantageously one can provide the host cells in a medium that desirably supports functioning and maintenance of the host cells (typically different from the environment used in the cells of the first plate for sequence amplification and modification). In an alternative embodiment, host cells are added to wells of the plate containing the expression cassette repertoire so that the sorted arrangement is retained (but this then does not provide the additional advantages of the other embodiment where a master plate of expression cassettes is retained without mixture with host cells—useful, for example, for carrying out a second transfer to another plate having a different type of host cell, such as when one wants to assess the performance of POI expression and display/secretion by a different host cell type).

An example of an automated multi-channel pipette is the Thermo Scientific Matrix Hydra II 96-Channel Automated Liquid Handling System. V&P Scientific VP 177AD-1 and VP 179BJD are dispensing manifolds designed for rapid filling of 96 and 384 well plates respectively, and either of these can be used in the method of the invention to transfer cassettes to host cells or for general sample handling.

The output of the method of the invention, therefore, in its broadest aspect is the production of a repertoire of host cells that expresses a repertoire of POIs. As discussed above, this can then be used in a subsequent step of screening (e.g., using a cell binding assay, ELISA, surface plasmon resonance or other assay appropriate for the particular nature of the POI) to identify one or more host cells that expresses a POI with a desired characteristic. One is then able to isolate POI from the cell or surrounding medium and/or isolate (and optionally replicate or amplify) a nucleotide sequence (e.g., DNA sequence) encoding the desired POI. The nucleotide sequence can be determined. Such isolated cells can be cultured to produce a POI-encoding cell line (which is especially useful when the cassette has been stably integrated into the cell genome, as is possible with site-directed genomic integration, e.g., performed using a transposon). The POI-encoding nucleotide sequence can be inserted into a different expression vector and/or mutated (e.g., affinity matured) or fused to another protein sequence.

Transposon integration is effected by providing a corresponding transposase enzyme in the host cells (e.g., by co-transfection of expression cassettes with a vector comprising an expressible transposase gene or by providing host cells that harbour such a tranposase gene, e.g., inducibly). In an example, each cassette comprises piggyBac transposon elements and the method uses a piggyBac transposase (e.g., wild-type or hyperactive piggyBac transposase; see, e.g., Yusa, K et al., PNAS USA, 2011, 10 (4):1531-1536; and Yusa K et al., "A hyperactive piggyBac transposase for mammalian applications", PNAS USA, 2010, 108(4):1531-1536).

WT PBase (SEQ ID NO: 57):

MGCSLDDEHILSALLQSDDELVGEDSDSEISDHVSEDDVQSDTEEAF

IDEVHEVQPTSSGSEILDEQNVIEQPGSSLASNRILTLPQRTIRGKN

KHCWSTSKSTRRSRVSALNIVRSQRGPTRMCRNIYDPLLCFKLFFTD

EIISEIVKWTNAEISLKRRESMTGATFRDTNEDEIYAFFGILVMTAV

RKDNHMSTDDLFDRSLSMVYVSVMSRDRFDFLIRCLRMDDKSIRPTL

RENDVFTPVRKIWDLFIHQCIQNYTPGAHLTIDEQLLGFRGRCPFRM

YIPNKPSKYGIKILMMCDSGTKYMINGMPYLGRGTQTNGVPLGEYYV

KELSKPVHGSCRNITCDNWFTSIPLAKNLLQEPYKLTIVGTVRSNKR

EIPEVLKNSRSRPVGTSMFCFDGPLTLVSYKPKPAKMVYLLSSCDED

ASINESTGKPQMVMYYNQTKGGVDTLDQMCSVMTCSRKTNRWPMALL

YGMINIACINSFIIYSHNVSSKGEKVQSRKKFMRNLYMSLTSSFMRK

RLEAPTLKRYLRDNISNILPNEVPGTSDDSTEEPVMKKRTYCTYCPS

KIRRKANASCKKCKKVICREHNIDMCQSCF

Hyperactive PBase (SEQ ID NO: 58):

MGSSLDDEHILSALLQSDDELVGEDSDSEVSDHVSEDDVQSDTEEAF

IDEVHEVQPTSSGSEILDEQNVIEQPGSSLASNRILTLPQRTIRGKN

KHCWSTSKPTRRSRVSALNIVRSQRGPTRMCRNIYDPLLCFKLFFTD

EIISEIVKWTNAEISLKRRESMTSATFRDTNEDEIYAFFGILVMTAV

RKDNHMSTDDLFDRSLSMVYVSVMSRDRFDFLIRCLRMDDKSIRPTL

RENDVFTPVRKIWDLFIHQCIQNYTPGAHLTIDEQLLGFRGRCPFRV

YIPNKPSKYGIKILMMCDSGTKYMINGMPYLGRGTQTNGVPLGEYYV

KELSKPVHGSCRNITCDNWFTSIPLAKNLLQEPYKLTIVGTVRSNKR

EIPEVLKNSRSRPVGTSMFCFDGPLTLVSYKPKPAKMVYLLSSCDED

ASINESTGKPQMVMYYNQTKGGVDTLDQMCSVMTCSRKTNRWPMALL

YGMINIACINSFIIYSHNVSSKGEKVQSRKKFMRNLYMGLTSSFMRK

RLEAPTLKRYLRDNISNILPKEVPGTSDDSTEEPVMKKRTYCTYCPS

KIRRKASASCKKCKKVICREHNIDMCQSCF

When a transposon is used for cassette integration in the host cell there are additional benefits. Firstly, transposons can integrate in several copies in host cells, thereby providing for multi-copy expression cassettes to support high level POI expression. This can be further promoted using a hyperactive transposase enzyme. Additionally, transposons can integrate preferentially at sites that are active for transcription, thereby also favouring high level and efficient POI expression as demonstrated by mapping analysis of integration sites. This is seen, for example, with piggyBac (see Wang W., et al., "Chromosomal transposition of PiggyBac in mouse embryonic stem cells", 2008, PNAS USA, 105(27): 9290-9295; Galvan D. L., et al., "Genome-wide mapping of PiggyBac transposon integration in primary human T cells", J. Immunother., 2009, 32(8): 837-844; and Yang W., et al., "Development of a database system for mapping insertional mutations onto the mouse genome with large-scale experimental data", 2009, BMC genomics, 10 (Suppl 3):S7).

Thus, the present invention provides the following concepts:

1. A method of producing cells encoding a repertoire of proteins of interest (POI), the method comprising:
    a) Providing a population of cells expressing a repertoire of POIs;
    b) Sorting the population of cells to produce a sorted population of single cells, each cell comprising nucleic acid encoding a respective POI;
    c) Amplifying the nucleic acid comprised by the sorted single cell population to produce a sorted repertoire of amplified nucleic acids encoding POIs;
    d) Modifying sorted amplified POI-encoding nucleic acids from step (c) to produce a sorted repertoire of expression cassettes, each cassette comprising a nucleotide sequence encoding a POI and one or more regulatory elements for expressing the POI; and
    e) Transferring POI expression cassettes from said cassette repertoire to a sorted population of host cells while maintaining the POI expression cassette sorting and producing a sorted repertoire of host cells that expresses a sorted repertoire of POIs.

Steps (c) and (d) can be carried out separately (in any order, e.g., (c) then (d)) or simultaneously.

Optionally, step (c) comprises PCR amplification of POI-encoding sequences, e.g., RT-PCR using POI-encoding mRNAs as template (e.g., one, two, three or more primers comprising or consisting of a sequence selected from the group consisting of SEQ ID NOs: 1-53, as discussed further below). Optionally, the repertoire of amplified nucleic acids in step (c) are DNAs. In an example, each POI is an antibody variable domain and step (c) comprises PCR amplification of POI-encoding sequences using one or more V region-specific 5' primers and/or one or more C region 3' primers (e.g., $C\gamma^-$, e.g., mouse $C\gamma^-$ primer). Optionally, the PCR comprises 5'- and/or 3'-RACE of POI-encoding nucleotide sequences. In an example, the 5'-RACE is carried out using one or more 5' primers each homologous to a 5' UTR or promoter sequence of an antibody variable region. In an example, the 3'-RACE is carried out using one or more 5' primers each homologous to an antibody constant region, e.g., a CH1 or Fc sequence. In this instance, each amplified POI-encoding sequence encodes an antibody chain comprising an antibody variable domain and constant region. In one example, the 3'-RACE uses one or more human constant region sequences as a primer; this then produces sequences encoding humanised variable regions in which each variable region is fused to a human constant region (e.g., a human gamma CH1 or Fc (e.g., gamma Fc)), thereby providing a human antibody chain (POI) upon subsequent expression. This humanisation during step (c) is useful since POIs identified from later screening represent human chains that can be used to produce antibody therapeutics for human use. In an example, the 5'-RACE uses a 5' template comprising a variable region promoter for producing amplified nucleic acids comprising (in 5' to 3' direction): a promoter and a nucleotide sequence encoding a POI. Additionally or alternatively, 3'-RACE is used, wherein the RACE uses a 3' template comprising a polyA sequence for producing amplified nucleic acids comprising (in 5' to 3' direction): a nucleotide sequence encoding a POI and a polyA. In this case, amplification and modification to produce expression cassettes can be carried out simultaneously (i.e., steps (c) and (d) are carried out simultaneously).

In an example, step (d) modification is carried out using PCR, e.g., bridge PCR. For example, step (d) is carried out after step (c), e.g., after RT-PCR or RACE amplification. In this case, bridge PCR is carried out in a step comprising hybridising a first primer to the 5' end of the nucleic acid products of step (c); and hybridising a second primer to the 3' end of the nucleic acid products of step (c) (or to the 3' end of the nucleic acid product of the hybridisation step using the first primer). Alternatively, the second primer can be used initially (to hybridise to the product of step (c)) and the product of that can be hybridised with the first primer. Alternatively, the first and second primers and product of step (c) can be mixed together and PCR carried out. The result in any case is an extended product comprising (in 5' to 3' order):

[5' sequence of the first primer]-[a promoter]-[a nucleotide sequence encoding a POI]-[a poly A]-[a 3' sequence of the second primer]

In one embodiment, the promoter and polyA are combined with the POI-encoding nucleotide sequence by step (c), as described above (e.g., using 5'- and 3'-RACE with appropriate primers). In another embodiment, the first primer used in step (d) comprises a promoter sequence (e.g., such a sequence at the 3' end of the primer). The result of step (d) then combines the promoter with the POI-encoding nucleotide sequence. Additionally or alternatively, the second primer used in step (d) comprises a polyA sequence (e.g., such a sequence at the 5' end of the primer). The result of step (d) then combines the polyA with the POI-encoding nucleotide sequence. Other combinations are possible, e.g., the promoter is added in step (c) using the appropriate primer and the polyA is added in step (d) using the appropriate second primer. In an example, step (c) (e.g., RACE) adds 5' and/or 3' sequences in the product nucleic acids that can be used for hybridisation with primers in a step (d) wherein the latter uses bridge PCR.

The result of steps (c) and (d) is always a repertoire of expression cassettes for expression of a repertoire of POIs. In an example, one or more regulatory elements required or desired for expression (or optimal expression) is omitted from each cassette, but is instead provided by the host cell genomes once the cassettes have been introduced into the host cells.

In an embodiment, step (d) adds 5' and 3' integration sequences flanking the promoter and polyA respectively. For example, the 5' sequence is a 5' transposon element (e.g., a 5' PB terminal element) and the 3' sequence is a 3' transposon element (e.g., a 3' PB terminal element that is in inverted orientation with respect to the 5' element). For example, the 5' integration sequence is provided at the 5' terminus of the first bridge PCR primer and/or the 3' integration sequence is provided at the 3' terminus of the second bridge PCR primer. The result is a repertoire of expression cassettes, each terminating (5' and 3') in tranposon elements, i.e., each cassette is modified to form a tranposon. Optionally, each expression cassette is produced as a linear DNA terminating at the 5' and 3' end by an integration sequence (e.g., a transposon element, e.g., terminating in inverted terminal PB transposon elements). Alternative integration sequences can be used instead of transposon elements (see further below); for example, the integration sequences can be homology arms (e.g., at least 15, 20, 50 or 100 contiguous nucleotides) for carrying out homologous integration into recipient host cell genomes at one or more specific target sites (that hybridise with the homology arms). Alternatively, the integration sequences can be site-specific recombination sequences (e.g., lox, rox or frt) for site-specific integration into host cell genomes carrying corresponding site-specific recombination sites at one or more desired integration sites in the genome (upon provision or expression of the respective integrase (i.e., cre, dre or flp respectively). In an embodiment, RMCE is used to insert using two incompatible recombination sites (e.g., wild type loxP and a mutant lox, e.g., lox2272 or lox511).

In one embodiment, one or more regulatory elements for POI expression (e.g., a promoter and/or and enhancer and/or a polyA and/or a signal sequence) is added by step (c), e.g. using RACE. Additionally or alternatively, one or more regulatory elements for POI expression (e.g., a promoter and/or and enhancer and/or a polyA and/or a signal sequence) is added by step (d), e.g. using bridge PCR.

Additionally or alternatively, in one embodiment, a 5' and/or a 3' integration sequence is added by step (c), e.g. using RACE. Additionally or alternatively, a 5' and/or a 3' integration sequence is added by step (d), e.g. using bridge PCR.

In an embodiment, one or more regulatory elements for POI expression (e.g., a promoter and/or and enhancer and/or a polyA and/or a signal sequence) and a 5' and/or a 3' integration sequence are added by step (c), e.g. using RACE.

In an embodiment, one or more regulatory elements for POI expression (e.g., a promoter and/or and enhancer and/or a polyA and/or a signal sequence) and a 5' and/or a 3' integration sequence are added by step (d), e.g. using bridge PCR.

2. The method of concept 1, wherein in step (e) the sorted expression cassettes are batch transferred to the sorted host cells.

Batch transferral according to this embodiment of the invention is superior to the prior art methods of using molecular cloning to transfer POI-encoding nucleotide sequences into host cells. As explained above, the latter requires laborious and time-consuming sequencing, analysis and subcloning of individual POI-encoding sequences that have been modified by the inclusion of terminal restriction sites (to enable introduction into host cells in subsequent steps). Typically, once a correct PCRd POI-encoding sequence with restriction sites has been confirmed, this is then selected as an individual sequence to take forward for introduction into host cells, the latter then being grown up to produce a population of cells expressing the chosen POI sequence. This process of multi-step, laborious molecular cloning is performed for each POI variant in a repertoire that is to be included in subsequent screening. Consequently, prior art screening methods can take several weeks (typically on the order of 6-8 weeks) to perform for a useful repertoire of starting cells, such as antibody producing cells. The method of the invention, in contrast, that uses sorted batch transferral of entire expression cassettes for POIs (i.e., including POI and regulatory elements for expression) provides a much faster technique for producing a sorted repertoire of POIs for screening. This makes the present method amenable to high-throughput automation of screening. For example, the present inventors—performing manual operation of the method—have been able to perform production of a sorted host cell repertoire for POI expression in only 2 days using 4×96-well plates (approximately 186 input B-cells). Screening of the expressed POI repertoire can be performed manually in around 2 days only. Clearly, automation speeds this up even more (and advantageously minimises cross-contamination between sorted aliquots).

For batch transferral of expression cassettes, a plurality of sorted expression cassettes are mixed in the same operation (e.g., a single cassette aspiration and delivery step, i.e., a single pipetting step) with the host cells for transferral into the cells (e.g., by subsequent or simultaneous transfection into the cells). That operation is, for example, a single transferral by pipette (e.g., using a multi-channel pipette, e.g., using a 4, 8, 12, 16, 64, 96, 384 or 1536 channel pipette in a single operation). In an example, at least 4 sorted aliquots of expression cassettes are mixed with sorted host cells in a single operation so that each expression cassette aliquot is mixed with a respective cell aliquot (e.g., in a respective container, e.g., a in a well of a plate or a tube in a rack). In an example, at least 4, 8, 12, 16, 24, 32, 40, 48, 56, 64, 96, 384 or 1535 sorted aliquots of expression cassettes are mixed in the same operation with sorted host cells so that each expression cassette aliquot is mixed with a respective cell aliquot (e.g., in a respective container, e.g., a in a well of a plate or a tube in a rack). In one embodiment, the operation is a manual operation (e.g., by pipetting using a multi-channel pipette). In another embodiment, the operation is automated, e.g., performed by an automated liquid handling apparatus (e.g., a liquid handling robot).

Advantageously, the inventors have found it possible to batch transfer the expression cassettes from step (d) to the sorted host cells without the need to purify the cassettes, but still yielding a useful host cell repertoire in step (e). This provides for higher processing speeds and throughput and makes the process amenable to simpler automation.

3. The method of concept 1 or 2, wherein (i) the sorted repertoire of expression cassettes produced by step (d) is provided in a plurality of containers whose locations relative to each other are fixed (e.g., wells on a plate or tubes in a rack), wherein each container contains a respective type of expression cassette such that the relative location of expression cassettes relative to each other is predetermined; and (ii) the expression cassettes are transferred to the sorted host cells in step (e) such that the relative locations of the expression cassettes is maintained.

In an example each container contains cassettes encoding a first type of POIs derived from a respective single cell provided in step (a) and also cassettes encoding a second type of POIs derived from said single cell. For example, each container contains cassettes encoding $V_H$ and $V_L$ sequences derived from a single cell. In this way the variable domains making up respective binding sites of input cells (where these encode antibody binding sites, e.g., plasmablasts or plasma cells) are kept together in the sorted repertoire but not mixed with sequences derived from another cell. This sorting is, thus, advantageously maintained in later steps of the process and is traceable in the result of the subsequent screening.

4. The method of any preceding concept, wherein (i) the repertoire of expression cassettes produced by step (d) is sorted by providing a plurality of containers (e.g., wells on a plate or tubes in a rack), wherein each container comprises POI-encoding sequences of a single cell sorted in step (b); (ii) the sorted host cells of step (e) are provided in a plurality of containers (e.g., wells on a plate or tubes in a rack) and (iii) the expression cassettes are transferred to the sorted host cells in step (e) such that host cells in each respective container are mixed only with POI-encoding sequences derived from a single cell sorted in step (b).

5. The method of concept 3 or 4, wherein in step (d) the sorted expression cassettes are provided in a plurality of containers whose locations relative to each other are fixed (e.g., a plurality of containers with an arrangement of X containers by Y containers, e.g., a 8×12 well plate (96-well plate) or a plate having a multiple of a 8×12 container arrangement (e.g., a 384 well plate)); and in step (e) the sorted host cells are provided in a plurality of containers whose locations relative to each other are fixed and comprise the same arrangement as the containers used in step (d) (e.g., the repertoires of steps (d) and (e) are both provided on 96-well or 384-well plates of the same or substantially the same dimension) so that sorting is maintained in step (e).

6. The method any preceding concept, wherein the sorted repertoire of host cells are capable of stably expressing the repertoire of POIs.

Alternatively, sorted repertoire of host cells are capable of transient expression. Stable expression (e.g., as a result of genomic integration of cassettes in host cell genomes) is advantageous for longer-term supply of cells—and thus expressed POIs—identified after screening (and also for cells while waiting to carry out screening if the host cells produced in step (e) are stored for a while before being used for screening).

7. The method of any preceding concept, wherein the sorted repertoire of POI-expressing host cells produced by step (e) is provided in a plurality of containers (e.g., tubes or wells), wherein each container contains POIs of a single cell sorted in step (b).

Such tubes may be fixed in a rack or holder; such wells may be fixed by provision on one or more plates.

8. The method of concept 7, wherein each host cell expresses first and second POIs, wherein the POIs are different, e.g., subunits of a protein, e.g., variable domains of an antibody or T-cell receptor binding site.

9. The method of any preceding concept, wherein step (b) comprises sorting single cells into respective containers (e.g., respective wells on one or more plates) and carrying out steps (c) and (d) in said containers while maintaining the sorting.

10. The method of any preceding concept, further comprising screening the sorted POI repertoire to identify a POI with a desired characteristic (e.g., binding to an antigen or antibody; or binding affinity for a cognate ligand or antigen) and/or a nucleotide sequence encoding the identified POI (e.g., DNA or RNA, e.g., mRNA or cDNA).

11. The method of concept 10, further comprising identifying, amplifying or synthesizing the nucleotide sequence encoding the identified POI (e.g., using PCR or by culturing a selected host cell or derivative cell thereof); and optionally producing isolated POI using said identified, amplified or synthesized nucleotide sequence.

12. The method of any preceding concept, further comprising screening the sorted POI repertoire to identify a POI with a desired characteristic (e.g., binding to an antigen or antibody; or binding affinity for a cognate ligand or antigen) and isolating a host cell expressing the identified POI; and optionally propagating the cell to produce a cell line expressing the POI.

13. The method of any preceding concept, wherein step (e) comprises genomically-integrating (e.g., chromosomally integrating) POI expression cassettes into respective host cell genomes for expressing the respective POIs. Alternatively, one or more of the cassettes is provided episomally in its respective host cell for transient POI expression.
14. The method of concept 13, wherein said genomic integration is carried out using a predetermined genomic nucleotide sequence motif for insertion of the expression cassettes into the respective cell genome.

For example, the motif is a nucleotide sequence used by a transposon for integration (e.g., the TTAA motif used by PB); or a nucleotide sequence that can recombine with cassette 5' and 3' integration sequences by homologous recombination; or a motif used to integrate a site-specific recombination site.
15. The method of concept 14, wherein each cell genome comprises more than one copy of the sequence motif.
16. The method of concept 13, 14 or 15, wherein said genomic integration is carried out by transposon-mediated integration.

Suitable transposon elements for use as 5' and 3' integration sequences of cassettes are class II transposon elements (e.g., piggyBac transposon inverted terminal repeat elements or Mariner transposon elements), or sleeping beauty transposon elements or Tc1-like elements (TLEs).
17. The method of any one of concepts 13 to 16, wherein step (e) comprises multiple insertions of expression cassettes into respective host cell genomes.

Each cassette is optionally provided as part of linear nucleic acid (e.g., linear DNA). For example, each cassette is a linear transposon comprising or consisting of 5'- and 3'-terminal transposon elements (e.g., piggyBac inverted terminal repeat elements) with POI nucleotide sequence and regulatory element(s) for expression between the transposon elements. In an embodiment, there is further sequence 5' of the 5' transposon element and/or 3' of the 3' transposon element; in another embodiment these elements are at the 5' and 3' termini of the cassette respectively.
18. The method of any preceding concept, wherein the host cells are cells of a mammalian cell line (e.g., CHO or HEK293 cells) or yeast cells.

For example, wherein each host cell is a mammalian (e.g., human or non-human animal, plant or insect or rodent or mouse or rat or rabbit or chicken or Camelid or fish cell), bacterial or yeast cell.
19. The method of any preceding concept, wherein in step (a) the cells are cells isolated from one or more animals.

Optionally, each cell of step (a) is a mammalian (e.g., human or non-human animal, plant or insect or rodent or mouse or rat or rabbit or chicken or Camelid or fish cell), bacterial or yeast cell.

Optionally, all cells of step (a) are cells of the same type of tissue or compartment of an organism(s). For example, they are all liver, kidney, heart, brain, blood, lymphocyte, prostate, ovary or germinal cells of one or more organisms, e.g., a human patient or a non-human animal, or a rodent or mouse or rat or rabbit or chicken or Camelid or fish.
20. The method of any preceding concept, wherein in step (a) the cells comprise or consist of B-cells, germinal centre cells, memory B-cells, antibody-secreting cells, plasma cells or plasmablast cells.
21. The method of any preceding concept, wherein each POI is an immunoglobulin (e.g., antibody or T-cell receptor) chain or part thereof (e.g., a variable domain).
22. The method of any preceding concept, wherein each POI comprises or consists of an antibody variable domain (e.g., a VH, VHH or VL domain or a dAb or Nanobody™).
23. The method of any preceding concept, wherein each cell of step (a) expresses first and second POIs, wherein the POIs are different from each other; wherein step (b) comprises sorting single cells into respective containers (e.g., respective wells on one or more plates) and carrying out steps (c) and (d) in said containers, wherein after step (c) each container comprises amplified first POIs mixed with amplified POIs from the same cell; and wherein step (e) comprises mixing respective first and second POI-encoding nucleic acids from a respective container with host cells; wherein first and second POIs from the same cell of step (a) are transferred to the same host cell for expression of first and second POIs by the host cell, thereby producing a repertoire of sorted host cells each co-expressing respective first and second POIs.
24. The method of concept 23, wherein the first and second POIs from the same cell are cognate polypeptides that together form a functional protein (e.g., $V_H$ and $V_L$ domains that form an antigen binding site).
25. The method of concept 24, wherein the first and second POIs comprise or consist of antibody $V_H$ and $V_L$ domains respectively, e.g., the first and second POIs are cognate antibody heavy and light chains respectively.
26. The method of any preceding concept, wherein step (b) comprises binding POIs expressed by cells to a cognate ligand (e.g., binding antibody binding sites expressed by cells to an antigen of interest); optionally wherein the ligand binds cell surface-expressed POI; and further sorting and isolating cells that express POIs that bind the ligand, thereby producing the sorted population of cells.
27. The method of concept 26, wherein FACS cell sorting is used; optionally fluorescence FACS.
28. The method of concept 26 or 27, wherein each sorted cell of step (b) is provided in a respective container (e.g., a well on a plate), such that each such container (e.g., well) comprises no more than one cell type.
29. The method of concept 28, wherein the sorted cell population is provided in wells on one or more plates comprising in total less than 5, 4, 3, 2, 1 or 0.5% wells containing more than one cell and/or in total less than 5, 4, 3, 2, 1 or 0.5% wells containing no cell.
30. The method of any preceding concept, wherein step (c) is performed using PCR, e.g., RT-PCR using POI-encoding RNA (e.g., mRNA).
31. The method of any preceding concept, wherein step (d) is performed using PCR, e.g., bridge PCR.
32. The method of any preceding concept, wherein step (d) comprises modification of amplified nucleic acids by combination with a predetermined sequence so that said predetermined sequence flanks 5' and/or 3' of POI-encoding nucleotide sequences of the nucleic acids; optionally wherein the modification places a regulatory element (e.g., a 5' promoter and/or a 3' polyA) and/or a transposon element (e.g., a piggyBac transposon element) flanking 5' and/or 3' of POI-encoding nucleotide sequences.
33. The method of concept 32, wherein each POI comprises an antibody variable domain and step (c) or (d) combines POI-encoding nucleotide sequences with an antibody constant region (optionally a human constant region or one of a species that is different to the species of C region comprised by POIs in the cells of step (a)) to produce a nucleotide sequence encoding an antibody chain (optionally a humanised chain).

For example, the cells of step (a) encode POIs comprising non-human vertebrate (e.g., rodent, e.g., mouse or rat) constant regions and these are replaced by human constant regions by step (c) or (d). For example the POIs are antibody chains (e.g., heavy chains) comprising a human variable domain and a rodent (e.g., mouse or rat) constant region that is humanised by the method of the invention. This is convenient since it provides a high-throughput way to humanise antibody chains and antibodies at scale and enables subsequent selection, production and cell and expression vector development in the context of final human antibody/chain formats suitable for human therapeutic drug use. Prior art techniques do not do this.

34. A method according to concept 33, further comprising screening the sorted POI repertoire to identify a host cell expressing an antibody chain with a desired characteristic (e.g., specific antigen binding or antigen binding affinity), identifying the antibody chain-encoding nucleotide sequence of the host cell, using the antibody chain-encoding nucleotide sequence to produce copies of the identified antibody chain, and formulating the copies as a pharmaceutical composition (optionally in combination with one or more further drugs, excipients, diluents or carriers) for human medical therapy; and optionally administering the composition to a human patient for medical therapy of the patient.

35. The method of any preceding concept, wherein step (e) is automated; optionally wherein one or all of steps (b) to (c) are also automated.

Automation may include control of the process by a computer programmed to carry out the method of any aspect, configuration, embodiment or example of the invention.

36. The method of any preceding concept, wherein (i) steps (b) to (e) inclusive are carried out in equivalent of at least 180 cells (provided in step (a) processed in no more than 1 or 2 days; and/or (ii) the repertoire of expressed POIs is screened for a desired characteristic and one or more corresponding host cells or POI-encoding nucleotide sequences are identified in an equivalent of no more than 4 days.

The inventors have achieved this using approximately 400 input B-cells and screening for antigen-specific antibodies, with (a) taking 2 days and (b) taking 3 days—all done manually. Clearly, this would be even faster if automation is used. Thus, the invention provides significant time saving over state of the art techniques that typically take 6-8 weeks to perform such screening.

37. An automated apparatus for performing the method of any preceding concept, the apparatus comprising
   a. Means for holding a sorted single cell population in a plurality of containers (e.g., wells on one or more plates, or tubes in a rack or holder as described above) wherein each single cell is in a respective container, each cell comprising nucleic acid encoding a respective POI;
   b. Means for delivering PCR reagents to the containers for amplifying nucleic acid comprised by the sorted single cell population to produce a sorted repertoire of amplified nucleic acids encoding POIs;
   c. Means for delivering to the containers reagents for modifying sorted amplified POI-encoding nucleic acids to produce a sorted repertoire of expression cassettes, each cassette comprising a nucleotide sequence encoding a POI and one or more regulatory elements for expressing the POI;
   d. Means for holding a sorted population of host cells in a plurality of containers;
   e. Means for transferring (optionally batch transferring) POI expression cassettes from said cassette repertoire to the sorted population of host cells in the containers while maintaining the POI expression cassette sorting; and
   f. Means for carrying out introduction (e.g., transfection) of expression cassettes into host cells in the containers to produce a sorted repertoire of host cells that expresses a sorted repertoire of POIs; and
   g. Optionally a computer programmed to carry out the method of any aspect, configuration, embodiment or example of the invention.

38. The apparatus of concept 37, further comprising means (e.g., means for performing FACS) for sorting a population of cells to produce the sorted population of single cells.

39. The apparatus of concept 37 or 38, further comprising means for controlling operation of the apparatus for automated performance of the method of any one of concepts 1 to 36.

40. A kit for carrying out the method of any one of concepts 1 to 36, the kit comprising an apparatus according to concept 37, 38 or 39 together with nucleic acid comprising transposon element(s) for performing the method of concept 32.

The transposon elements can be carried by, e.g., linear DNA. In an example, the elements are elements of a transposon that mediates DNA integration by a cut-and-paste transposition mechanism (e.g., Class II transposon). In an example, the elements are PB or Mariner-like elements or Tc-1-like elements (TLEs).

41. An expression cassette for expression of a POI in a host cell, the cassette being provided by linear nucleic acid (e.g., linear DNA) comprising a transposon, the transposon comprising 5'- and 3'-terminal transposon elements with a POI-encoding nucleotide sequence and regulatory element(s) for POI expression between the transposon elements.

Such cassettes are useful for genomically-integrating expressible POI sequences into host cells, e.g., for producing a cell line to provide a POI source and/or for use in the screening method of the invention. The transposon elements can be any such elements disclosed herein.

In an example, the cassette comprises or consists of a transposon comprising 5'- and 3'-terminal transposon elements (e.g., piggyBac inverted terminal repeat elements) with a POI-encoding nucleotide sequence and one or more regulatory element(s) for expression between the transposon elements. In an embodiment, the cassette comprises a further sequence 5' of the 5' transposon element and/or 3' of the 3' transposon element. In an example, the cassette comprises an additional nucleotide sequence corresponding to a nucleotide sequence of the host cell genome, said additional sequence being 5' and/or 3' of the POI-encoding nucleotide sequence. For example, the additional sequence corresponds to genomic host cell sequence that is actively transcribed in the host. Thus, the POI-encoding sequence is inserted into the host in an environment suited to active transcription of the POI sequence.

In an example, a "population" (e.g., a population of cells or cassettes) or "repertoire" as used herein comprises at least 10, 100, 1000, $10^4$, $10^5$ or $10^6$ members.

42. A population of expression cassettes according to concept 41, wherein the population encodes a repertoire of POIs.

43. A sorted population of expression cassettes according to concept 42.
44. A sorted population of expression cassettes encoding a repertoire of POIs corresponding to POIs expressed by a population of cells, each cassette comprising a nucleotide sequence encoding a member of the repertoire of POIs and one or more regulatory elements for POI expression (when in a host cell), wherein each said cassette comprises the arrangement (in 5' to 3' direction): transposon element-[POI nucleotide sequence & regulatory element(s)]-transposon element, and expression cassettes for expression of POIs corresponding to POIs of different cells are isolated from each other in the sorted population (e.g., in different wells of a plate, e.g., one cassette species per well on one or more plates).

In an example, each cassette is capable of expressing a POI of (derived from) a single cell, e.g., an antibody heavy or light chain or fragment thereof derived from a single B-cell.

In an example, piggyBac elements are used.

45. The population of concept 44, wherein each expression cassette is provided by a linear DNA.
46. The cassette population of any one of concepts 42 to 45, wherein each cassette is in a host cell.
47. A sorted population of host cells comprising the sorted population of expression cassettes according to any one of concepts 43, 44 and 45 for expression of a sorted repertoire of POIs.
48. A method of making a transposon comprising a nucleotide sequence of interest (NOI), the method comprising
    a. Providing a first nucleotide sequence (e.g., provided by DNA or RNA) comprising (in 5' to 3' direction) A, B and C (optionally consisting of the structure 5'-A-B-C-3'), wherein A is a first homology sequence, B is a nucleotide sequence comprising (or consisting of) the NOI and C is a second homology sequence;
    b. Providing a first template nucleotide sequence comprising (or consisting of) (in 5' to 3' direction) W and X, wherein W is a nucleotide sequence comprising (or consisting of) a first transposon element (e.g., a piggyBac terminal repeat element) and X is a third homology sequence; and
    c. Providing a second template nucleotide sequence comprising (or consisting of) (in 5' to 3' direction) Y and Z, wherein Y is a fourth homology sequence and Z is a nucleotide sequence comprising (or consisting of) a second transposon element (e.g., a piggyBac terminal repeat element); and either
    d. (i) Mixing the first nucleotide sequence with the first template to hybridise the first and third homology arms together and carrying out nucleic acid amplification and extension (e.g., using PCR) to extend the first nucleotide sequence using the first template to produce a first extended nucleotide sequence (first ENS) comprising (in 5' to 3' direction) W, B and C; and (ii) mixing the first ENS with the second template to hybridise the second and fourth homology arms together and carrying out nucleic acid amplification and extension to extend the first ENS to produce a second ENS comprising (or consisting of) (in 5' to 3' direction) W, B and Z; or
       (ii) Mixing the first nucleotide sequence with the second template to hybridise the second and fourth homology arms together and carrying out nucleic acid amplification and extension (e.g., using PCR) to extend the first nucleotide sequence using the second template to produce a third extended nucleotide sequence (third ENS) comprising (in 5' to 3' direction) A, B and Z; and (ii) mixing the third ENS with the first template to hybridise the first and third homology arms together and carrying out nucleic acid amplification and extension to extend the third ENS to produce a fourth ENS comprising (or consisting of) (in 5' to 3' direction) W, B and Z; or
       (iii) Mixing the first nucleotide sequence with the first and second templates to hybridise the first and third homology arms together and to hybridise the second and fourth homology arms together and carrying out nucleic acid amplification and extension (e.g., using PCR) to extend the first nucleotide sequence using the second template to produce a fifth ENS comprising (or consisting of) (in 5' to 3' direction) W, B and Z; and
    e. Isolating an ENS comprising (or consisting of) (in 5' to 3' direction) W, B and Z, thereby producing an isolated transposon comprising a NOI flanked by transposon elements; and
    f. Optionally introducing the isolated transposon into a recipient cell so that the transposon integrates into the genome of the cell.

Optionally one, more or all of the homology sequences comprises a nucleotide sequence of at least 10, 20, 30, 40, 50, 60, 70, 80, 90, 100, 150, 200 or more contiguous nucleotides.

In an example, the NOI encodes a POI, protein domain or protein fragment or is itself one or more regulatory element(s). For example the NOI encodes a POI that is an orthologue or homologue of a protein in the recipient cell genome or in a human or non-human vertebrate.

In an embodiment, W and X are at the 5' and 3' termini of the first template sequence respectively. Additionally or alternatively, Y and Z are at the 5' and 3' termini of the second template sequence respectively. When W and X are at the 5' and 3' termini of the first template sequence respectively and Y and Z are at the 5' and 3' termini of the second template sequence respectively, the product of the method is a linear transposon with transposon elements at its termini which is well suited to genomic integration to modify host cells.

Optionally the first template consists of 5'-W-X-3'. In an example, there is no intervening nucleotide sequence between W and X. In another embodiment, there is a further nucleotide sequence between W and X, e.g., a regulatory element or exon or other desired nucleotide sequence (e.g., protein-coding sequence) which will become combined immediately upstream of the NOI in the product of the method. This is useful, for example for constructing an expression cassette for combining a promoter upstream of a NOI (where the NOI encodes a POI) for subsequent expression of the POI once the transposon has been inserted into a host cell genome.

Additionally or alternatively, optionally the second template nucleotide sequence consists of 5'-X-Y-3' or there is an intervening nucleotide sequence between X and Y, e.g., a regulatory element or exon or other desired nucleotide sequence (e.g., protein-coding sequence) which will become combined immediately downstream of the NOI in the product of the method. This is useful, for example for constructing an expression cassette for combining a polyA downstream of a NOI (where the NOI encodes a POI) for subsequent expression of the POI once the transposon has been inserted into a host cell genome. In another example, the intervening sequence encodes a protein that will become fused to the POI upon expression to produce a fusion product. For example, the POI comprises or consists of an antibody variable domain and the intervening sequence comprises or consists of an antibody constant region-encoding sequence. For example, the intervening sequence encodes an antibody Fc or an antibody CH1 or CL domain. In an example, the Fc or constant region or protein encoded by the intervening sequence is a human Fc, constant region or protein. This is useful for humanising the POI (e.g., to produce a humanised antibody chain when the POI is a variable domain, e.g., a human variable domain).

49. The method of concept 48, wherein there is an intervening nucleotide sequence between W and X and/or an intervening nucleotide sequence between Y and Z; optionally wherein the or each intervening sequence is a regulatory element or protein-coding sequence.

50. The method of concept 49, wherein the NOI encodes a protein domain (e.g., an antibody variable domain) and there is a nucleotide sequence encoding an antibody constant region (e.g., an antibody Fc, e.g., a human Fc) between Y and Z, whereby the transposon product encodes a fusion protein comprising a protein domain fused to an antibody constant region (e.g., encoding an antibody chain).

51. The method of any one of concepts 48 to 50, wherein one or more of the first and second homology arms is combined with the NOI by PCR (e.g., 5'- and/or 3'-RACE) to form said first nucleotide sequence before carrying out said extension.

52. A method of making a repertoire of transposons, wherein members of the repertoire encode different POIs (e.g., different antibody variable domains), the method comprising
i. Providing a population of first nucleotide sequences comprising a repertoire of NOIs; and
ii. For each first nucleotide sequence, carrying out the method of any one of concepts 48 to 51, thereby producing a repertoire of transposons encoding a repertoire of POIs.

53. The method of concept 52, comprising sorting the first nucleotide sequences to provide a sorted population before carrying out step (ii), wherein a sorted repertoire of transposons is produced encoding a sorted repertoire of POIs.

54. The method of concept 52, wherein the transposons of said repertoire of transposons are mixed together.

55. The method of any one of concepts 52 to 54, wherein transposons of the repertoire are introduced into recipient cells so that transposons integrate into the genome of cells, each integrated transposon comprising a POI expression cassette flanked by transposon elements, the cassette comprising a NOI and one or more regulatory elements for expression of the POI in a host cell.

56. The method of concept 55 when dependent from concept 53, wherein the sorting is maintained when the transposons are introduced into the cells, thereby producing a sorted repertoire of cells expressing a sorted repertoire of POIs.

57. A method of producing a host cell for expression of a POI, the method comprising
a. Providing at least first and second expression cassettes, wherein each expression cassette comprises
i. a first integration element and a second integration element 3' of the first integration element nucleotide sequence; and
ii. between the integration elements a nucleotide sequence encoding a POI and one or more regulatory elements for expressing the POI;
iii. wherein the integration elements are capable of insertion into a nucleic acid by recognition of a predetermined nucleotide sequence motif of the nucleic acid using an integration enzyme;
b. Providing a host cell whose genome comprises a plurality of said motifs; and
c. Simultaneously or sequentially introducing the first and second expression cassettes into the host cell, wherein each cassette is genomically-integrated in the host cell genome at a said motif for expression of POIs by the host cell; and
d. Optionally producing a cell line expression POIs in a step comprising culturing the host cell.

This aspect of the invention is useful for producing host cells and cell lines for relatively high expression of one or more POIs of interest. Genomic integration of POI cassettes at multiple genomic sites provides for stable expression and there is also the possibility to target transcriptionally-active regions of the host genome. Use of sequence motifs guides the insertion to useful sites and this is preferable to random integration of sequences as used in the art.

58. The method of claim 57, wherein the first and second integration elements of the first cassette are identical to the first and second integration elements respectively of the second cassette.

In an example, each cassette comprises first and second transposon elements, e.g., elements of the same type of transposon (e.g., PB or a Class II transposon). In an example, all elements are site-specific recombination sites, e.g., lox sites or frt sites or a mixture of these. In another example, all elements are homology arms (contiguous nucleotide sequences sufficient for homologous recombination in the host cell). In an example, the site-specific recombination sites are the same or they are different (e.g., mutually incompatible sites (e.g., loxP and lox511 or 2272) for carrying out RMCE (recombinase-mediated cassette exchange) for directed insertion of the cassette into the genome.

59. The method of claim 57 or 58, wherein the first and second integration elements of each of said first and second cassettes are in mutually inverted orientation (e.g., inverted PB transposon elements or inverted site-specific recombination sites).

60. The method of any one of claims 57 to 59, wherein one or more of said motifs is engineered into the chromosome of the host cell prior to carrying out step (c), e.g., lox site pairs are engineered into one or more host chromosomes, wherein pairs corresponding to lox pairs in cassettes are used).

61. The method of any one of claims 57 to 59, wherein one or more of said motifs is endogenous to the host cell genome; optionally wherein each of said motifs at which a cassette is integrated is an endogenous motif.

For example, transposons recognise endogenous motifs (e.g., PB recognises TTAA in genomes).

62. The method of any one of claims 57 to 61, wherein at least 3 cassettes are genomically-integrated into the host cell genome, e.g., into one or more host chromosomes—which is useful for stable expression.

63. The method of any one of claims 57 to 62, wherein the cassette genomic integration sites are active for transcription of the POI-encoding sequences.

This can be achieved using transposons (e.g., PB) in the cassettes.

64. The method of any one of claims 57 to 63, wherein each cassette is integrated by homologous recombination between the integration sites and the host genome; site-specific recombination between the integration sites and the host genome; or by transposon-mediated integration.

65. The method of claim 64, wherein the enzyme is selected from a recombinase or a transposase (e.g., an enzyme corresponding to the integration elements PBase (e.g., hyperactive PBase), flp or cre recombinase).

In an example, the host cell has been engineered to express such enzyme(s), e.g., from a genomically-integrated gene (e.g., an inducible gene). In another embodiment, the enzyme is expressed from an episomal vector. In another example, the enzyme is introduced into the host cell.

66. The method of any one of claims 57 to 64, wherein each cassette is a transposon.

67. The method of any one of claims 57 to 66, comprising providing a population of host cells and carrying out the method of any one of claims 57 to 66 on a plurality of host cells of said population; and optionally isolating the host cells produced by step (c) or (d).

68. The method of any one of claims 57 to 67, comprising isolating a host cell produced by step (c) or (d) and identifying, amplifying or synthesizing the nucleotide sequence encoding the POI expressible by the cell; and optionally producing isolated POI using said identified, amplified or synthesized nucleotide sequence or a mutant thereof.

69. The method of claim 68, comprising formulating the isolated POI into a drug for human medicine; and optionally administering the drug to a human patient.

70. A population of host cells obtainable by the method of any one of claims 57 to 69, each cell comprises a plurality of genomically-integrated expression cassettes for expressing POIs, each host cell comprising a plurality of identical nucleotide sequence motifs throughout its genome adjacent an integrated expression cassette for expression of a POI from each such cassette; each integrated cassette comprising
   a. a first integration element sequence and a second integration element sequence 3' of the first integration element nucleotide sequence; and
   b. between the integration element sequences a nucleotide sequence encoding a POI and one or more regulatory elements for expressing the POI.

71. The host cells of claim 70, wherein all POIs expressed by the cells are the same POI.

72. The host cells of claim 70, wherein the cells express first and second POIs (e.g., VH and VL domains of a single antibody type; or heavy and light chains of a single antibody type) that associate together to form a functional protein or ligand (e.g., antigen) binding site.

73. An antibody or antigen binding site of an antibody for medical treatment of a human, wherein the antibody or binding site has been isolated from a host cell produced by a method of any one of claims 57 to 69 or isolated from a host cell of a population according to any one of claims 70 to 72.

74. A nucleic acid mixture comprising a first isolated nucleic acid and a second isolated nucleic acid, wherein the first nucleic acid is capable of hybridising to a human antibody V region 5'UTR sequence (i.e., a nucleotide sequence) of a gene comprised by a target nucleic acid, wherein the gene encodes a human V region; and the second nucleic acid is capable of hybridising to a second sequence, wherein the second sequence is comprised by the target nucleic acid and is 3' to the UTR sequence, wherein the first isolated nucleic acid comprises (or consists of) a sequence that is at least 90, 91, 92, 93, 94, 95, 96, 97, 98 or 99% % identical (or 100% identical) to a sequence selected from the group consisting of SEQ ID NOs: 1-47.

SEQ ID NOs: 1-47 comprises human variable region-specific sequences as indicated in Table 1 (more particularly specific 5'UTR nucleotide sequences of human variable regions). By "specific to" is meant that such sequences can be used as a 5' primer sequence in standard PCR (e.g., RT-PCR) of human variable region nucleic acid.

SEQ ID NOs: 1-17 comprises human heavy chain variable region-specific sequences.

SEQ ID NOs: 18-26 comprises human kappa chain variable region-specific sequences.

SEQ ID NOs: 27-47 comprises human kappa chain variable region-specific sequences.

In an embodiment, the invention provides a nucleic acid (e.g., a PCR primer or a vector for homologous recombination) comprising (or consisting of) at least 15 contiguous nucleotides of a Sequence denoted X in Table 2 for hybridising to the 5'UTR sequence of a gene segment denoted Y in Table 2, e.g., for performing PCR to copy the gene segment or to hybridise a homologous recombination vector to the 5'UTR sequence for modification of the gene segment. In an example, the nucleic acid comprises (or consists of) at least 15, 16, 17, 18, 19, 20, 21, 22, 23, 24 or 25 or all of sequence X. In an example, the contiguous nucleotides end with the 3' nucleotide of sequence X (i.e., the contiguous nucleotides extending 5' from the 3' end of X are used). In an embodiment, the invention provides a mixture of two or more of the nucleic acids, e.g., for PCR copying of two or more variable region sequences (e.g., using DNA, cDNA or RNA from corresponding B-cells). In an example, two, more or all of the nucleic acids in the mixture copy $V_H$ gene segments. In an example, two, more or all of the nucleic acids in the mixture copy $V_\lambda$ gene segments. In an example, two, more or all of the nucleic acids in the mixture copy Vκ gene segments. Optionally, the, or each, nucleic acid comprises a promoter nucleotide sequence immediately 5' of the UTR sequence (or the 15 or more contiguous nucleotide part). For example, the promoter sequence is a CMV promoter sequence as follows:

(SEQ ID NO: 54)
5'-CTTACTGGCTTATCGAAATTAATACGACTCAGATC-3'

In an example, the invention provides:
A PCR primer or homologous recombination vector comprising at least 15 contiguous nucleotides of a human antibody variable gene segment UTR sequence for hybridising to the 5'UTR sequence of an antibody variable gene segment denoted Y in Table 2, wherein the primer/vector sequence is selected from the group consisting of the sequences denoted X in Table 2.

In an example of the nucleic acid, mixture or primer of the invention, each nucleic acid or primer hybridises with its cognate sequence at a temperature of from such as 45-70° C., (e.g., at 50° C., or 60° C., or 68° C.) or 60-75° C., in a PCR reaction. A person skilled in the art will be aware of cycle times and temperatures to carry out the PCR reaction.

Each nucleic acid of the invention and mixture of the invention is useful for performing PCR amplification or replication of a target nucleotide sequence encoding a human antibody variable domain or a protein comprising such a domain, for example PCR of human variable region-encoding nucleotide sequence(s) isolated from one or more cells (e.g., B-cells). Thus, in an embodiment, each nucleic acid is a PCR primer.

Each nucleic acid of the invention and mixture of the invention is useful for performing homologous recombination to modify a target nucleotide sequence (e.g., a sequence comprised by the genome of a cell, e.g., a mammalian cell, e.g., an ES cell or CHO cell). For homologous recombination, as is known by the skilled person, one uses a nucleic acid vector comprising a 5' homology arm, a 3' homology arm and optionally a predetermined nucleotide sequence of interest therebetween. The sequence can, for example, encode a POI, a protein domain or be comprise a regulatory element. In an alternative there is no intervening sequence between the homology arms (and in this case the vector is used to delete sequence from the genome lying between regions that hybridise with the homology arms, as is known by the skilled person). In the present embodiment, the invention provides a homologous recombination vector, wherein the vector comprises a 5' arm comprising a 3' homology arm and optionally a nucleotide sequence therebetween, wherein the 5' arm comprises (or consists of) a sequence that is at least 90, 91, 92, 93, 94, 95, 96, 97, 98 or 99% identical to a sequence selected from the group consisting of SEQ ID NOs: 1-47 (or is 100% identical) and/or wherein the 3' arm comprises (or consists of) a sequence that is at least 90, 91, 92, 93, 94, 95, 96, 97, 98 or 99% identical (or is 100% identical) to a sequence selected from the group consisting of SEQ ID NOs: 48 to 53. This enables gene targeting of specific V and/or C gene segments of Ig loci in a vertebrate using homologous recombination.

The invention, therefore, also provides a method of modifying an Ig locus comprised by a vertebrate cell, the method comprising introducing the vector of the invention into the cell (e.g., by transfection) and carrying out homologous recombination to modify the Ig locus; and optionally expressing an antibody V domain or chain from the modified locus. Optionally, the sequence of the V domain is identified or copied or isolated from the cell and used to produce an antibody or a pharmaceutical composition comprising such an antibody for human medical use.

The invention further provides a PCR primer that comprises (or consists of) a sequence that is at least 90, 91, 92, 93, 94, 95, 96, 97, 98 or 99% % identical to a sequence selected from the group consisting of SEQ ID NOs: 1-53 (or is 100% identical). For example, the primer is in vitro.

The term "isolated" excludes sequences that are present in the chromosomal content of vertebrate or a vertebrate cell.

The nucleic acid, PCR primer or mixture may be provided in vitro, e.g., mixed with a PCR buffer or reagent. In an example, a nucleic acid, primer or mixture of the invention is provided in a container, a vial, a tube, a dish or a PCR cuvette.

Optionally, the first isolated nucleic acid comprises (or consists of) a sequence that is at least 90, 91, 92, 93, 94, 95, 96, 97, 98 or 99% identical to a sequence selected from the group consisting of SEQ ID NOs: 1-47. Optionally, the first isolated nucleic acid comprises (or consists of) a sequence selected from the group consisting of SEQ ID NOs: 1-47.

75. The mixture of concept 74, wherein the first isolated nucleic acid comprises a sequence that is least 90, 91, 92, 93, 94, 95, 96, 97, 98 or 99% identical to a sequence selected from the group consisting of SEQ ID NOs: 1-17.

Optionally, the first isolated nucleic acid comprises a sequence selected from the group consisting of SEQ ID NOs: 1-17.

76. The mixture of concept 74, wherein the first isolated nucleic acid comprises a sequence that is least 90, 91, 92, 93, 94, 95, 96, 97, 98 or 99% identical to a sequence selected from the group consisting of SEQ ID NOs: 18-26.

Optionally, the first isolated nucleic acid comprises a sequence selected from the group consisting of SEQ ID NOs: 18-26.

77. The mixture of concept 74, wherein the first isolated nucleic acid comprises a sequence that is least 90, 91, 92, 93, 94, 95, 96, 97, 98 or 99% identical to a sequence selected from the group consisting of SEQ ID NOs: 27-47.

Optionally, the first isolated nucleic acid comprises a sequence selected from the group consisting of SEQ ID NOs: 27-47.

78. The mixture of any one of concepts 74 to 77, wherein the second isolated nucleic acid comprises an antibody constant region sequence; optionally a sequence that is at least 90, 91, 92, 93, 94, 95, 96, 97, 98 or 99% identical to a sequence selected from the group consisting of SEQ ID NOs: 48 to 53.

Optionally, the second isolated nucleic acid comprises a sequence selected from the group consisting of SEQ ID NOs: 48 to 53. SEQ ID NOs: 48-51 are sequences from mouse constant regions; SEQ ID NOs: 52 and 53 are sequences from human constant regions (see Table 1).

79. The mixture of concept 75, wherein the second isolated nucleic acid comprises an antibody heavy chain constant region sequence; and optionally comprises a sequence that is at least 90, 91, 92, 93, 94, 95, 96, 97, 98 or 99% identical (or 100% identical) to SEQ ID NO: 48 or 49.

80. The mixture of concept 76, wherein the second isolated nucleic acid comprises an antibody kappa chain constant region sequence; and optionally comprises a sequence that is at least 90, 91, 92, 93, 94, 95, 96, 97, 98 or 99% identical (or 100% identical) to SEQ ID NO: 50 or 51.

81. The mixture of concept 77, wherein the second isolated nucleic acid comprises an antibody lambda chain constant region sequence; and optionally comprises a sequence that is at least 90, 91, 92, 93, 94, 95, 96, 97, 98 or 99% identical (or 100% identical) to SEQ ID NO: 52 or 53.

82. A nucleic acid mixture comprising a first isolated nucleic acid and a second isolated nucleic acid, wherein the nucleic acids are different and selected from nucleic acids comprising a sequence that is at least 90, 91, 92, 93, 94, 95, 96, 97, 98 or 99% identical (or 100% identical) to a sequence selected from the group consisting of SEQ ID NOs: 1-47.

In an example, the nucleic acids are PCR primers; in another embodiment they comprise homologous recombination vectors for modifying an Ig locus or loci.

83. The mixture of concept 82, comprising a sequence selected from the group consisting of SEQ ID NOs: 18-26 and a sequence that is at least 90, 91, 92, 93, 94, 95, 96, 97, 98 or 99% identical (or 100% identical) to a sequence selected from the group consisting of SEQ ID NOs: 18-26 and/or selected from the group consisting of SEQ ID NOs: 27-47.

84. The mixture of concept 82 or 83, wherein each of the first and second isolated nucleic acids is selected that is at least 90, 91, 92, 93, 94, 95, 96, 97, 98 or 99% identical (or 100% identical) to a sequence selected from the group consisting of SEQ ID NOs: 1-17.

85. The mixture of concept 84, comprising at least 3 different isolated nucleic acids each that is at least 90, 91, 92, 93, 94, 95, 96, 97, 98 or 99% identical (or 100% identical) to a sequence selected from the group consisting of SEQ ID NOs: 1-17.
86. The mixture of concept 82 or 83, wherein each of the first and second isolated nucleic acids is at least 90, 91, 92, 93, 94, 95, 96, 97, 98 or 99% identical (or 100% identical) to a sequence selected from the group consisting of SEQ ID NOs: 18-26.
87. The mixture of concept 84, comprising at least 3 different isolated nucleic acids that each is at least 90, 91, 92, 93, 94, 95, 96, 97, 98 or 99% identical (or 100% identical) to a sequence selected from the group consisting of SEQ ID NOs: 18-26.
88. The mixture of concept 82 or 83, wherein each of the first and second isolated nucleic acids is at least 90, 91, 92, 93, 94, 95, 96, 97, 98 or 99% identical (or 100% identical) to a sequence selected from the group consisting of SEQ ID NOs: 27-47.
89. The mixture of concept 84, comprising at least 3 different isolated nucleic acids each that is at least 90, 91, 92, 93, 94, 95, 96, 97, 98 or 99% identical (or 100% identical) to a sequence selected from the group consisting of SEQ ID NOs: 27-47.
90. The mixture of concept 84 or 85, wherein the mixture comprises an antibody heavy chain constant region sequence; and optionally comprises SEQ ID NO: 48 and/or 49.
91. The mixture of concept 86 or 87, wherein the mixture comprises an antibody kappa chain constant region sequence; and optionally comprises SEQ ID NO: 50 and/or 51.
92. The mixture of concept 87 or 88, wherein the mixture comprises an antibody lambda chain constant region sequence; and optionally comprises SEQ ID NO: 52 and/or 53.
93. The method of any one of concepts 1 to 36, wherein step (c) is performed by PCR using one or more mixtures according to any one of concepts 74 to 92.
94. The method of any one of concepts 48 to 56, wherein the method is performed by PCR using one or more mixtures according to any one of concepts 74 to 92.
95. A kit comprising one or more mixtures according to any one of concepts 74 to 92 and an apparatus according to any one of concepts 36 to 39.
96. A method of amplifying a repertoire of human variable region sequences, the method comprising
   a. Providing a population of cells expressing a repertoire of human variable regions, wherein the cells comprise nucleotide sequences encoding the variable regions;
   b. Replicating a plurality of said variable region-encoding nucleotide sequences using PCR and PCR templates; and
   c. Isolating, sequencing or identifying one or more of the replicated nucleotide sequences or carrying out steps (d) and (e) of the method of any one of concepts 1 to 36;
      wherein one or more templates of step (b) comprises a sequence that is at least 90, 91, 92, 93, 94, 95, 96, 97, 98 or 99% identical (or 100% identical) to a sequence selected from the group consisting of SEQ ID NOs: 1-52.
97. The method of concept 96, wherein step (b) uses one or more mixtures according to any one of concepts 74 to 92 as PCR template.
98. The method of concept 96 or 97, wherein the cells in step (a) are sorted single cells (e.g., sorted into wells of one or more plates).
99. The method of concept 96 or 97, further comprising producing a human variable region (e.g., as part of an isolated antibody chain or an isolated antibody for human medicine) using a replicated sequence obtained in step (c) and optionally producing a cell line that expresses the human variable region.

The following optional features are applicable to any configuration, aspect, embodiment or example of the invention described herein.

Optionally, the POI-encoding nucleotide sequence is operably linked to a promoter capable of driving expression of the POI, wherein the promoter comprises a eukaryotic promoter that is regulatable by an activator or inhibitor. In another embodiment, the eukaryotic promoter is operably linked to a prokaryotic operator, and the eukaryotic cell optionally further comprises a prokaryotic repressor protein.

Optionally, each expression cassette comprises a sequence encoding a marker, such as a selectable marker, e.g., a hygromycin resistance gene or encoding a fluorescent protein (e.g., the fluorescent protein is selected from DsRed, GFP, eGFP, CFP, eCFP, and YFP).

Optionally, one or more or all of the expression cassettes comprises first and second POI-encoding nucleotide sequences, e.g., in tandem or as a bicistronic cassette. In an example, the encoded POIs are different (e.g., VH and VL of an antibody); in another example, they are different. In an example, 1, 2, 3, 4, 5, 6 or more POI-encoding nucleotide sequences.

In an example, the or each host cell is a CHO (Chinese Hamster Ovary) cell or HEK293 cell.

For example, the protein of interest can be an antibody or fragment thereof, a chimeric antibody or fragment thereof, an ScFv or fragment thereof, an Fc-tagged protein or fragment thereof, a growth factor or a fragment thereof, a cytokine or a fragment thereof, or an extracellular domain of a cell surface receptor or fragment thereof.

Nucleic Acid Constructs

Recombinant expression cassettes (vectors) can comprise synthetic or cDNA-derived DNA fragments encoding a protein of interest, operably linked to a suitable transcriptional and/or translational regulatory element derived from mammalian, viral or insect genes. Such regulatory elements include transcriptional promoters, enhancers, sequences encoding suitable mRNA ribosomal binding sites, and sequences that control the termination of transcription and translation. Mammalian expression cassettes can also comprise non-transcribed elements such as an origin of replication, other 5' or 3' flanking non-transcribed sequences, and 5' or 3' non-translated sequences such as splice donor and acceptor sites. A selectable marker gene to facilitate recognition of transfectants may also be incorporated.

Transcriptional and translational control sequences in expression cassettes useful for transfecting vertebrate cells may be provided by viral sources. For example, commonly used promoters and enhancers are derived from viruses such as polyoma, adenovirus 2, simian virus 40 (SV40), and human cytomegalovirus (CMV). Viral genomic promoters, control and/or signal sequences may be utilized to drive expression, provided such control sequences are compatible with the host cell chosen. Non-viral cellular promoters can also be used (e.g., the beta-globin and the EF-1 alpha promoters), depending on the cell type in which the recombinant protein is to be expressed.

DNA sequences derived from the SV40 viral genome, for example, the SV40 origin, early and late promoter, enhancer, splice, and polyadenylation sites may be used to provide other genetic elements useful for expression of the heterologous DNA sequence. Early and late promoters are particularly useful because both are obtained easily from the SV40 virus as a fragment that also comprises the SV40 viral origin of replication (Fiers et al., Nature, 1978, 273:113). Smaller or larger SV40 fragments may also be used. Typically, the approximately 250 by sequence extending from the Hind III site toward the BglI site located in the SV40 origin of replication is included.

Bicistronic expression vectors used for the expression of multiple transcripts have been described previously (Kim S. K. and Wold B. J., Cell, 1985, 42:129) and can be used in combination with one or more POI-encoding sequences.

Host Cells and Transfection

Optionally, eukaryotic host cells are used in the methods of the invention, e.g., they are mammalian host cells, including, for example, CHO cells or mouse cells.

Expressed proteins (POIs) will preferably be secreted into the culture medium, depending on the nucleic acid sequence selected, but may be retained in the cell or deposited in the cell membrane. Various mammalian cell culture systems can be employed to express recombinant proteins. Examples of suitable mammalian host cell lines include the COS-7 lines of monkey kidney cells, described by Gluzman (1981) Cell 23:175, and other cell lines capable of expressing an appropriate vector including, for example, CV-1/EBNA (ATCC CRL 10478), L cells, C127, 3T3, CHO, HeLa and BHK cell lines. Other cell lines developed for specific selection or amplification schemes will also be useful with the methods and compositions provided herein. A preferred cell line is the CHO cell line designated K1. In order to achieve the goal of high volume production of recombinant proteins, the host cell line is optionally pre-adapted to bioreactor medium in the appropriate case.

Several transfection protocols are known in the art, and are reviewed in Kaufman (1988) Meth. Enzymology 185: 537. The transfection protocol chosen will depend on the host cell type and the nature of the POI, and can be chosen based upon routine experimentation. The basic requirements of any such protocol are first to introduce DNA encoding the protein of interest into a suitable host cell, and then to identify and isolate host cells which have incorporated the heterologous DNA in a relatively stable, expressible manner.

One commonly used method of introducing heterologous DNA into a cell is calcium phosphate precipitation, for example, as described by Wigler et al. (Proc. Natl. Acad. Sci. USA 77:3567, 1980). DNA introduced into a host cell by this method frequently undergoes rearrangement, making this procedure useful for cotransfection of independent genes.

Polyethylene-induced fusion of bacterial protoplasts with mammalian cells (Schaffner et al., (1980) Proc. Natl. Acad. Sci. USA 77:2163) is another useful method of introducing heterologous DNA. Protoplast fusion protocols frequently yield multiple copies of the plasmid DNA integrated into the mammalian host cell genome, and this technique requires the selection and amplification marker to be on the same nucleic acid as the pOI.

Electroporation can also be used to introduce DNA directly into the cytoplasm of a host cell, for example, as described by Potter et al (Proc. Natl. Acad. Sci. USA 81:7161, 1988) or Shigekawa et al (BioTechniques, 6:742, 1988). Unlike protoplast fusion, electroporation does not require the selection marker and the POI to be on the same nucleic acid.

More recently, several reagents useful for introducing heterologous DNA into a mammalian cell have been described. These include Lipofectin™ Reagent and Lipofectamine™ Reagent (Gibco BRL, Gaithersburg, Md.). Both of these reagents are commercially available reagents used to form lipid-nucleic acid complexes (or liposomes) which, when applied to cultured cells, facilitate uptake of the nucleic acid into the cells.

A method for amplifying the POI is also desirable for expression of the recombinant protein, and typically involves the use of a selection marker (reviewed in Kaufman supra). Resistance to cytotoxic drugs is the characteristic most frequently used as a selection marker, and can be the result of either a dominant trait (e.g., can be used independent of host cell type) or a recessive trait (e.g., useful in particular host cell types that are deficient in whatever activity is being selected for). Several amplifiable markers are suitable for use in the expression vectors of the invention (e.g., as described in Maniatis, Molecular Biology: A Laboratory Manual, Cold Spring Harbor Laboratory, N Y, 1989; pgs 16.9-16.14).

Useful selectable markers for gene amplification in drug-resistant mammalian cells are shown in Table 1 of Kaufman, R. J., supra, and include DHFR-MTX resistance, P-glycoprotein and multiple drug resistance (MDR)-various lipophilic cytotoxic agents (e.g., adriamycin, colchicine, vincristine), and adenosine deaminase (ADA)-Xyl-A or adenosine and 2'-deoxycoformycin.

Other dominant selectable markers include microbially derived antibiotic resistance genes, for example neomycin, kanamycin or hygromycin resistance. However, these selection markers have not been shown to be amplifiable (Kaufman, R. J., supra,). Several suitable selection systems exist for mammalian hosts (Maniatis supra, pgs 16.9-16.15). Co-transfection protocols employing two dominant selectable markers have also been described (Okayama and Berg, Mol. Cell Biol 5:1136, 1985).

Useful regulatory elements, described previously or known in the art, can also be included in the nucleic acid constructs used to transfect mammalian cells. The transfection protocol chosen and the elements selected for use therein will depend on the type of host cell used. Those of skill in the art are aware of numerous different protocols and host cells, and can select an appropriate system for expression of a desired protein, based on the requirements of the cell culture system used.

An aspect provides a pharmaceutical composition comprising an isolated POI (e.g., antibody, chain or variable domain) and a diluent, excipient or carrier, optionally wherein the composition is contained in an IV container (e.g., and IV bag) or a container connected to an IV syringe and wherein the POI has been isolated from a host cell of the invention or population of host cells.

An aspect provides the use of the POI of the invention in the manufacture of a medicament for the treatment and/or prophylaxis of a disease or condition in a patient, e.g. a human.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

Example 1

Figure 1B:
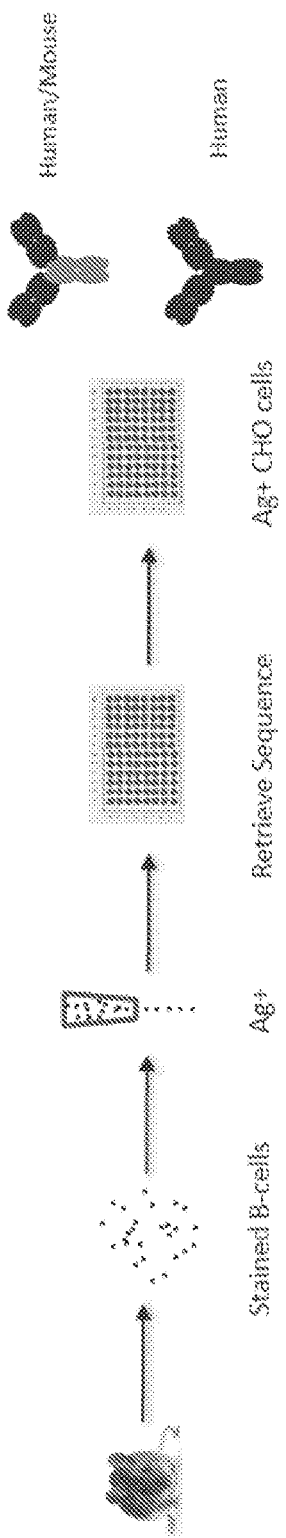
FIG. 1B is an alternative schematic illustrating a non-limiting example of the method of the invention for producing a repertoire of antibody binding sites (POIs) in host cells (e.g., CHO or HEK293 cells).
Figure 2:
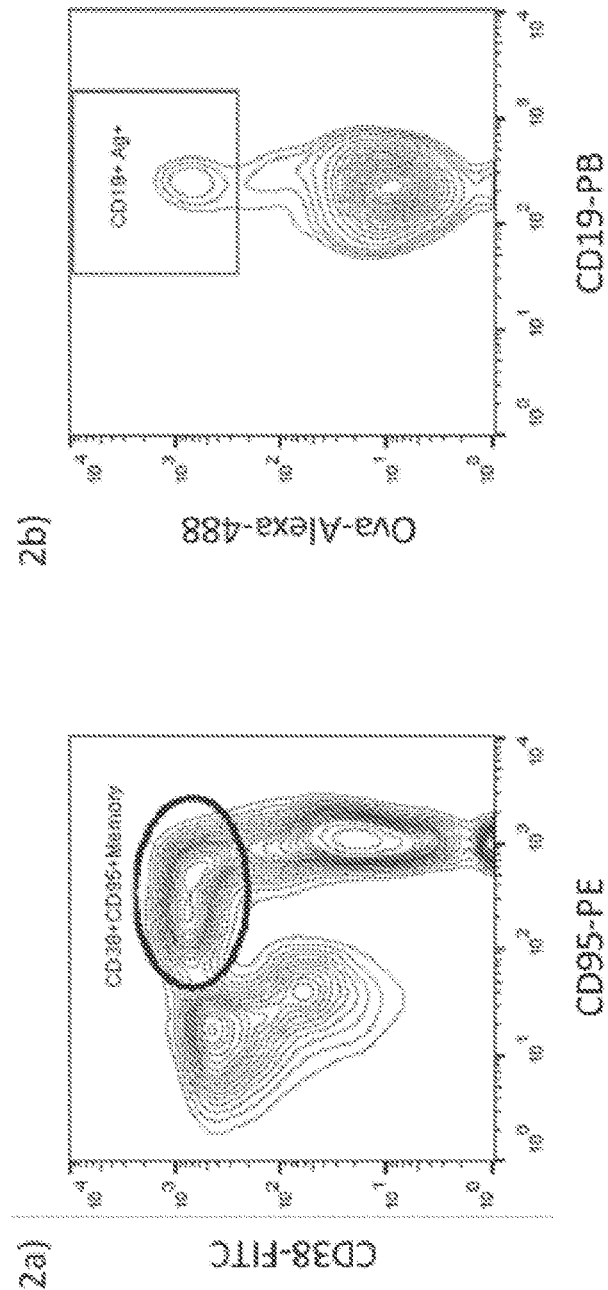
FIG. 2: Examples of gating strategy for different populations of B cells. (a) An example of a flow cytometric contour plot displaying the gating of CD38+CD95+ memory cell population after the exclusion of IgM and IgD B cells. (b) Each individual memory cell positive for CD19 (Pacific Blue) and antigen (Ovalbumin-AlexaFluor-488) is then sorted into separate wells in a 96-well plate.

The B cell cloning technology of the present invention includes three major steps—isolation of antigen-specific single B cells or ASCs from spleen, lymph node and bone marrow with corresponding cell markers; antibody sequence rescue from single cells and expression cassette amplification; expression of recombinant antibodies in mammalian cells. The flow chart is shown in FIG. 1B. The details of each step are described below Example 1A: Isolation of Antigen-Specific Single Cells Antigen-specific cells include the memory/GC cells with membrane-bound antibody and the antibody-secreting plasma cells. A panel of cell surface markers were used to define and label mouse memory/GC cells (CD19; IgM; IgD; CD38; CD95) (FIG. 2). Antigen specific cells were stained using fluorescence-labelled soluble antigens (for example, any small molecule fluorophore which can be detected by the cell sorting system, such as Alexa-488, Alexa-647, Pacific Blue, R-phycoerythrin, fluorescein isothiocyanate, or allophycocyanin optionally conjugated to a cyanine dye, e.g. Cy7) or cell surface antigens in virus-like particles (VLPs). FIG. 2 is an example of labelling the antigen specific memory/GC cells in OVA immunized mouse spleen. Over 10,000 OVA-specific memory/GC IgG cells could be sorted from one spleen. Single-cell sorting was performed using a BD influx flow cytometer equipped with an automatic cell deposition unit. FACS-sorted cells were deposited into 96-well PCR plates with lysis buffer for the next step.

Figure 3:
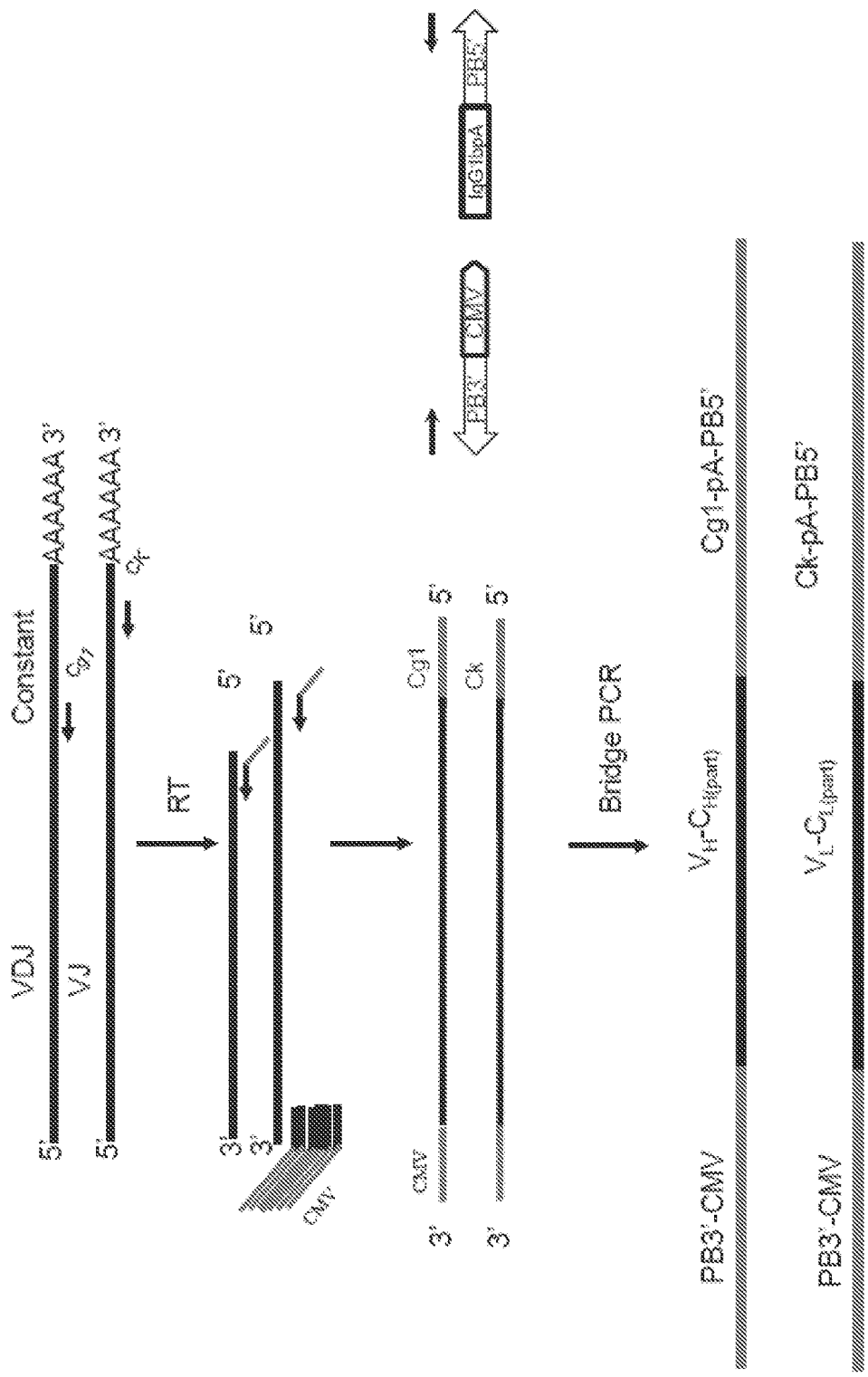
FIG. 3: A flowchart summarizing the high-throughput production of antibodies from single B cells. Single cell-based cDNA synthesis was performed using constant region-specific primers. Mixture of V gene-specific primers for heavy chain and light chain with a human cytomegalovirus (hCMV) promoter fragment at the 5' end were used for the first round PCR to amplify the V gene fragment. A generic forward primer that annealed to the hCMV tag was used with a reverse nested primer for the constant region for the second round PCR. The amplified products were then bridged with linear Ig-cassette with 5' PB LTR-CMV promoter and constant region-polyA signal-3' PB LTR.

Generally, antigen-specific GC (germinal centre) or memory B cells can be captured by labelled antigen because they dominantly express transmembrane antibodies on the cell surface. On the other hand, plasmablast or plasma cells were thought to be less easily captured by labelled antigen because of their dominant expression of secreting antibody. We next attempted to isolate ASPCs using fluorescently labelled antigen and anti-CD138 to sort the cells from the rest of the cell population using FACS (FIG. 3). As shown in FIG. 2, the majority of isolated antigen-specific plasma or plasmablast cells but none of those left-over same types of cells showed that they were antigen-specific ASCs in the ELISPOT assay. This demonstrated that the cell sorting method using fluorescence-labelled antigen can efficiently capture all the antigen-specific ASCs probably with residual transmembrane antibodies or temporary anchoring secreted antibody on the cell surface.

The fluorescently-labelled antigen can be replaced with VLPs with recombinant antigen on its surface. The VLPs are generated from CHO cells, KEK cells, MEFs (mouse embryonic fibroblasts) or other mammalian cell lines with co-expression of the recombinant antigen, the retrovirus gag protein, and MA-GFP (gag matrix fragment p15-GFP fusion protein). The gag expression enables VLP budding from cells, and the MA-GFP labels the VLPs for fluorescence detection. Both gag and MA-GFP proteins are associated with the inner surface of the plasma membrane, and recombinant antigen is on the VLP surface. The antigens on the VLPs are presented on native form directly expressed from recombinant cells without any step of purification or modification. The native form of an antigen should provide all the natural epitopes which greatly help selection of neutralizing antibodies. The high density of the antigen on the VLPs increases the signal/noise ratio for detection of cells expressing antigen-specific antibodies on the cell surface and greatly facilitates the sorting step. The recombinant VLPs can be generated with expression of different fluorescent proteins such as MA-CFP or MA-YFP. Using multiplexing of VLPs with different antigen and different fluorescence protein, cells expressing high affinity binders, cross-reactive binders or homolog-specific binders can be selected. The cells expressing high affinity binders can be selected by cells with relative high affinity matrix (affinity matrix=the ratio of binding activity to low density antigen over to high density antigen VLPs). The cells expressing cross-reactive binders to orthologs or different antigens (for 2-in-1 bi-specific antibody isolation) can be selected by cells binding to different types of VLPs at the same time. The cells expressing homolog-specific binders also can be selected by cell only binding to specific antigen but not its homolog.

Example 1B: High-Throughput Recovery of the Antibody Sequence from Single Cells

A rapid, efficient and high-throughput method was developed for generation of antibody from individual B cells without any molecular cloning step. The method allowed us to produce Ig-expression constructs from amplified variable gene segments of heavy chain and light chain from a single cell (FIG. 3). Through the whole PCR procedure, heavy chain and light chains from a single cell were amplified in the same well.

The sequences of antibody V regions were recovered by RT-PCR and two rounds of PCRs by the following procedure. Single-cell sorted plates stored at −80° C. were thawed on ice and briefly centrifuged before use. Plates were incubated in the thermal cycler at 65° C. for 5 minutes and indefinitely at 4° C. 6 μL mixture of primers, Superscript III, dNTP, RNase inhibitor and buffer were added to each well and mixed by pipetting. Plates were briefly centrifuged and incubated at 50° C. for 60 minutes. Constant region specific primers for the heavy chain and light chain were used to amplify the variable gene segments from single cell. Gene-specific reverse primers were used to amplify the kappa, lambda, and gamma chains were gamma RT1, kappa RT1, and lambda RT3.

The first round of PCR was performed with forward V gene-specific primers with a human cytomegalovirus (hCMV) promoter fragment at the 5' end, and reverse constant region-specific primers. Product from the RT-PCR was used as template for the first PCR. The PCR product comprises the variable immunoglobulin region and part of the constant region. Cycling conditions for the first PCR included an initial denaturation step at 98° C. for 30 minutes, followed by 13 touchdown cycles of 98° C. for 10 minutes, 72° C. to 60° C. for 30 minutes and 72° C. for 30 minutes with a drop of 1° C. for each subsequent annealing step; 20 cycles of 98° C. for 10 minutes, 60° C. for 30 minutes and 72° C. for 30 minutes, followed by a final extension at 72° C. for 2 minutes and held at 4° C. indefinitely.

Figure 4:
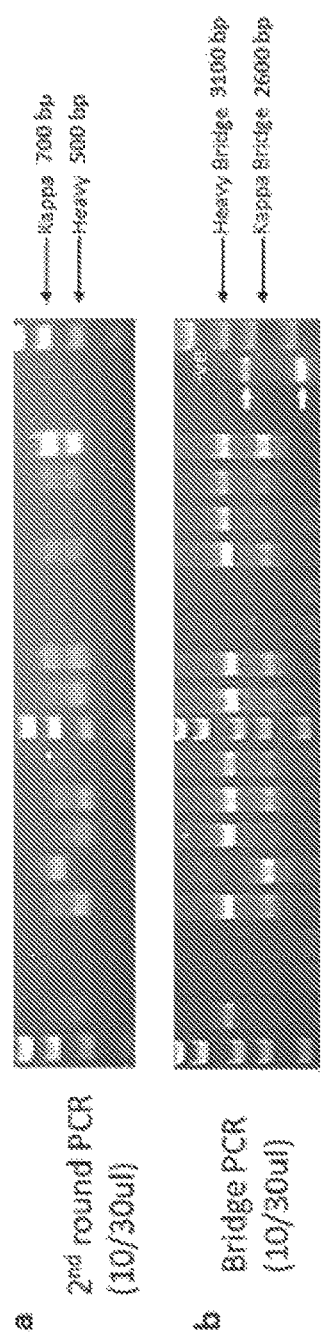
FIG. 4: Production of heavy and light chain expression constructs by bridge PCR. (a) Ethidium bromide-stained agarose gels of the pairs of $V_H$ and $V_L$ gene fragments amplified from single B cells. Each lane contains 10 µL of a 30 µL $V_H$+$V_L$ second round PCR product. (b) Ethidium bromide-stained agarose gels showing the bridge PCR results. Each lane contains 10 µL of a 30 µL bridge product for Ig-expression. The negative controls showed the Ig-cassette of heavy and light chains. Representative PCR products from the high-throughput 96-well PCR platform were shown here.

In the second round of PCR, a generic forward primer that annealed to the hCMV tag was used with a reverse nested primer for the constant region. 1 µL of the products from the first PCR were used as templates for the nested second PCR. Cycling conditions for the second PCR included an initial denaturation step at 98° C. for 30 minutes, followed by 20 cycles of 98° C. for 10 minutes, 68° C. for 30 minutes, and 72° C. for 30 minutes; a final extension at 72° C. for 2 minutes and held at 4° C. indefinitely. ⅓ of the second round PCR product were run in 1% Agarose gel to check the recovery rate of the antibody sequence from single cells for RT and 2 rounds of PCR steps. Since the primers for heavy and light chain were mixed into the same wells, the PCR products contain two bands representative for heavy chain VDJ region and light chain VJ region. The expected sizes of PCR products are ~700 bp for the kappa and lambda light chains, and ~500 bp for the gamma heavy chain (FIG. 4a).

For antibody expression in the mammalian cells, the amplified products were then bridged with linear Ig-cassette with 5' PB LTR-CMV promoter and constant region-polyA signal-3' PB LTR (FIG. 3). The Ig-cassette contains all essential elements for expression of the antibody, including the CMV promoter, the immunoglobulin chain constant region and the poly (A) signal. Additionally, the cassette has long overlapping regions of CMV and constant region homology on its ends. 2 µL of the products from the second round PCR were used as template for the bridge PCR. Cycling conditions for the bridge PCR were an initial denaturation step at 98° C. for 30 minutes, followed by 5 cycles of 98° C. for 10 minutes, 68° C. for 30 minutes, and 72° C. for 2 minutes; and 25 cycles of 98° C. for 10 minutes, 60° C. for 30 minutes, and 72° C. for 2 minutes; followed by a final extension at 72° C. for 2 minutes and held at 4° C. indefinitely. ⅓ of the bridge PCR product were run in 1% Agarose gel to check the recovery rate of bridge PCR. The expected sizes of PCR products are ~2600 bp for the kappa and lambda light chains, and ~3100 bp for the gamma heavy chain (FIG. 4b).

The bridge step allows bringing of all the expression elements and PB LTRs together to form the PB transposon with heavy chain and light chain expression genes. No matter which isotype the mouse antibodies have, mouse IgG1, IgG2a, IgG2b, IgG3 or human IgG1, IgG2, IgG3, IgG4 or any variants of constant region can be applied in the bridge step to reformat the Fc. The method applied in this technology does not require any purification step and can be extensively automated. The overall recovery rate for the B-cell technology (BCT) through cell sorting and single cell PCR is about 38-71% for different cell populations (Table 3).

Example 1C: Sequence Analysis by Clusters

Figure 5:
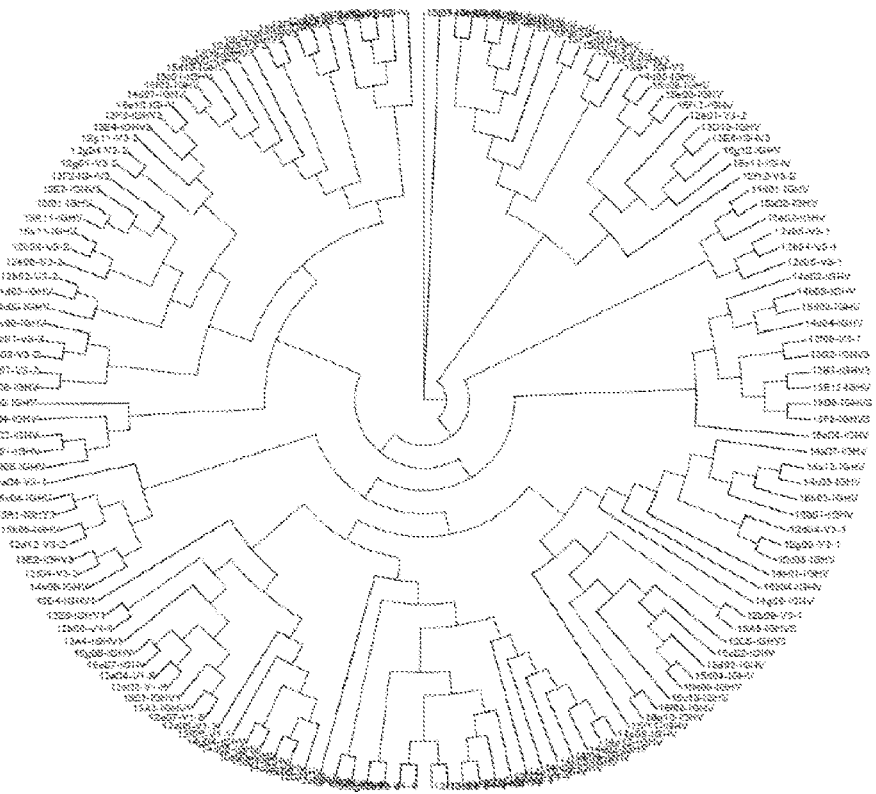
FIG. 5: Analysis of the antibody sequences of the sorted Ag-specific single B-cells from project 1. The antibody sequences expressed by individual B cells were arranged by heavy-chain V-gene family usage and clustered to generate the displayed phylogenetic trees.

The second round PCR products were sent for sequencing. The nucleotide sequences were was determined using an Applied Biosystems 373 DNA sequencer. The sequences were analysed by the Kymab seq-utils program (Lee E. C. et al, Nature Biotechnol., 2014, 32:356-363.). The program predicts germline sequence and the hypermutation of the analysed IG sequence. The variable immunoglobulin region comprises a VDJ region of an immunoglobulin nucleotide sequence for heavy genes and a VJ region of an immunoglobulin nucleotide sequence for Igκ and IgA. A clonal family is generally defined by the use of related immunoglobulin heavy chain and/or light chain V(D)J sequences by 2 or more samples. Related immunoglobulin heavy chain V(D)J sequences can be identified by their shared usage of V(D)J gene segments encoded in the genome (FIG. 5).

Figure 6:
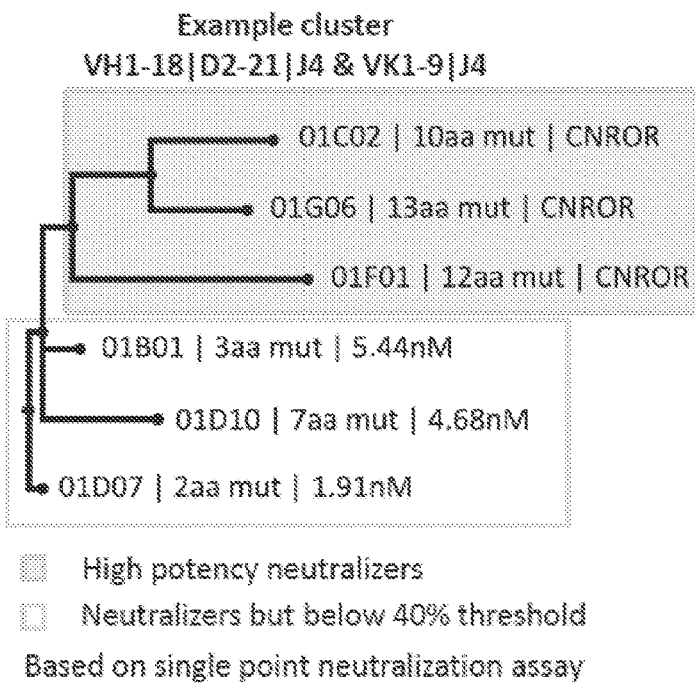
FIG. 6: An example of clustered family which showed the affinity maturation via hypermutation for both apparent affinity and neutralization potency. CNROR: unable to resolve off rate.

Within a clonal family, there are generally subfamilies that vary based on shared mutations within their V(D)J segments, that can arise during B-cell gene recombination and somatic hypermutation. Clones with different V(D)J segment usage usually exhibit different binding characteristics. Also, clones with the same V(D)J segment usage but different mutations exhibit different binding characteristics. B cells undergo somatic hypermutation, where random changes in the nucleotide sequences of the antibody genes are made, and B cells whose antibodies have a higher affinity B cells are selected (FIG. 6). If low affinity clones from the same lineage have neutralization function, the potency usually increases in clones with more mutation to acquire higher affinity.

Example 1D: Generation of Monoclonal Antibodies from Single Cells

Figure 7:
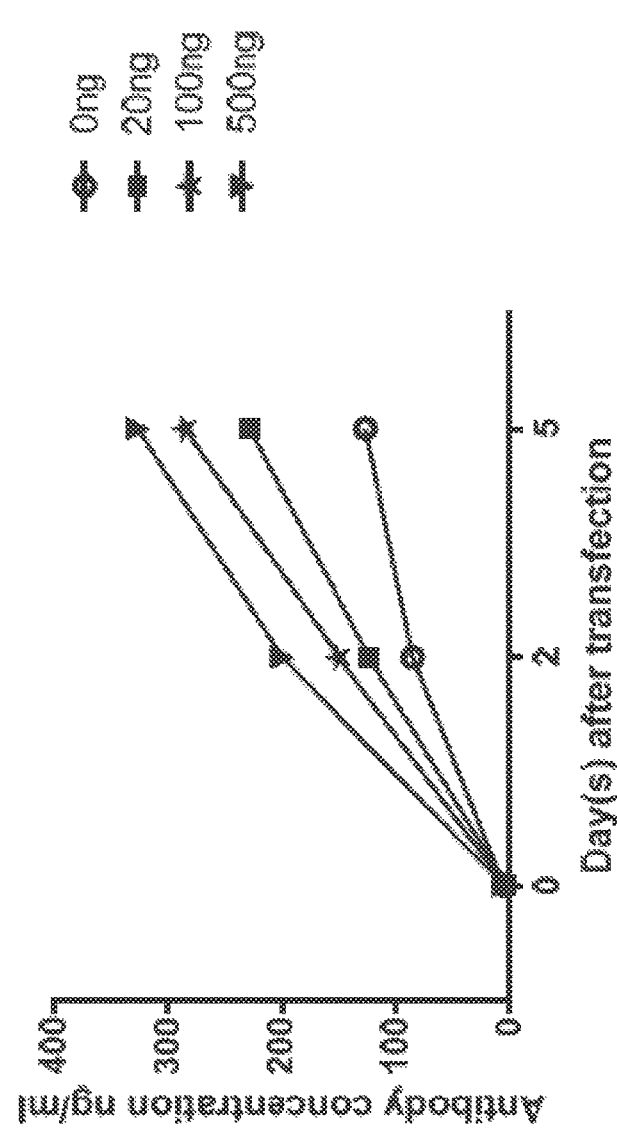
FIG. 7: Expression level boosted by PiggyBac transposon system. Antibody expression of the transfected bridge PCR products in HEK293 cells was tested using co-transfection with different amount of PBase: 0; 20; 100; 500 ng/well. Supernatants in each well were collected on day 0; day 2; and day 5. Data showed that the transposon system increased the expression level by 2-4 times on day 5.

The final PCR step amplified the linear expression cassette encoding heavy chain and light chain. The amplified cassettes for heavy chain and light chain, and the PB transposase (PBase) expression vector were co-transfected into mammalian cell line without purification and cloning. Supernatant with transient or stable expression of antibody were then collected in the corresponding time points. Transfection of the conventional expression vector likely causes concatemer integration into genome and the integrated gene is subject to being silenced. PB transposon-mediated expression provides a major advantage for high and stable expression level of transfected genes because multiple copies (10-100) of PB transposons can be transposed and integrated to genome within the transcription-active regions, allowing high level expression of antibody (FIG. 7).

Figure 8:
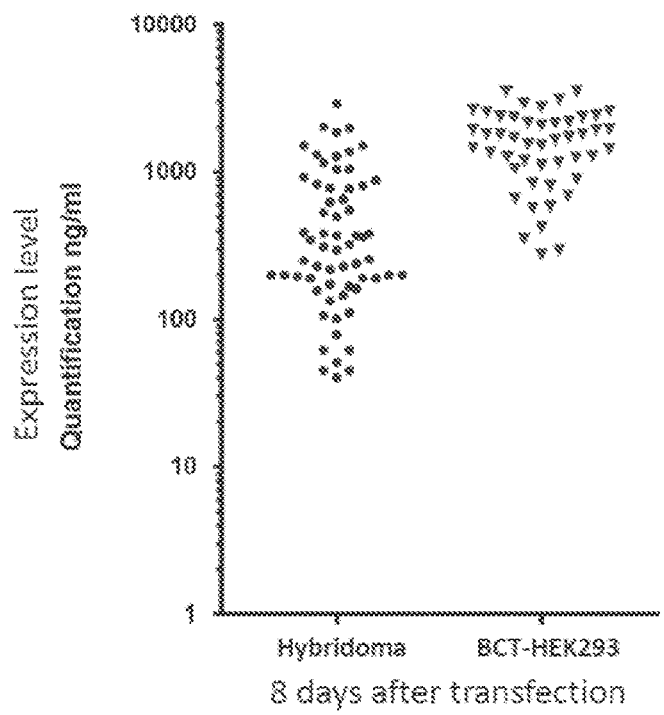
FIG. 8: Example of quantification of the IgG concentration in supernatant of HEK293 cells transfected with bridge PCR products. The concentration was determined by a sandwich ELISA eight days after the transfection. The concentration is from about 200 ng/mL to 3000 ng/mL which is comparable to the concentration in the supernatant of prior art hybridoma technologies.

Transfections of bridge PCR products and PBase expression vectors for transient expression were done using Lipofectamine 2000 following the manufacturer's protocol. Transfections were carried out in 96-well deep well plates. In brief, HEK293 cells were cultured in DMEM+10% ultralow IgG FBS (Invitrogen) to prevent bovine IgG from competing with secreted human IgG at the downstream protein A purification step. For 96-well plate transfections, each well was seeded the day before with $5 \times 10^5$ cells in 500 µL of medium, and allowed to grow to $1 \times 10^6$ cells the next day. 25 µL out of the 30 µL of the bridge PCR products were incubated in Optimem media with 100 ng of PBase vector for a final volume of 70 uL, and Lipofectamine 2000 was also separately incubated with 70 uL of Optimem media. Both incubations were for 10 minutes. Lipofectamine 2000 and the PCR products were then mixed by gentle pipetting and incubated for 15 minutes before adding to HEK293 cells and gently mixed. Culture supernatants were collected on day 8 after transfection for following screenings. The IgG concentration in supernatants containing antibodies of interest is determined by IgG ELISA (FIG. 8). The concentration of the expressed antibodies is comparable to what we normally get from the hybridoma technology which is enough to most of the downstream screens for the antibody binding ability or functional assays. The overall hit rates for B cell technology through cell sorting to IgG identification is 36%-71% depending on different cell populations (Table 3).

Example 1E: Antibody-Binding Screening Assay Using LI-COR Odyssey NIR Scanning

The expressed antibodies from the HEK293 cell transfection of the B-cell technology (BCT) were first screened for their ability to bind to the antigen of interest using LI-COR Odyssey NIR scanning, and then positive clones were screened for their apparent affinity by Surface Plasmon Resonance (ProteOn XPR36, BioRad) (see below).

B cells producing antigen-specific antibodies were identified by fluorescent screening. Each well of clear 384-well flat-bottom plates was seeded with $1 \times 10^4$ adherent CHO cells stably transfected with a gene encoding a human transmembrane antigen in 80 μL of F12 medium containing 10% (v/v) FBS ($1.25 \times 10^5$ cells/mL) using a Multidrop instrument. Cells were incubated overnight at 37° C. in a $CO_2$ incubator. The next day the culture media was removed by aspiration and 45 μL of LI-COR IRDye 800CW anti-Mouse antibody added at 500 ng/mL+5 mM DRAQ5 (LI-COR) diluted 1:25,000 in FACS Buffer (PBS+1% BSA+ 0.1% $NaN_3$). 5 μL of BCT supernatant, 5 μL of control antibody (2 μg/mL) in HEK293 culture medium or 5 μL of mouse IgG1 control antibody (Sigma, 2 μg/mL) in HEK293 culture medium was added using a FluidX liquid handler. Plates were incubated for 1 hr at 4° C. and culture media aspirated. The reaction was stopped and the cells fixed by the addition of 25 μL of 4% paraformaldehyde per well and incubation for 15 minutes at RT. Plates were washed twice with 100 μL of PBS and the wash solution was removed by blotting on paper towels. Plates were scanned using a Li-Cor Odyssey Classic instrument. The overall hit rates for BCT through cell sorting to Antigen specific identification is 25%-61% depending on different cell populations (Table 3).

TABLE 3

Recovery rate of each steps of B-cell technology

| BCT procedures | Recovery rate | | | |
|---|---|---|---|---|
| | Spleen memory/ GC cells | LN memory/ GC cells (RIMMS) | Spleen Plasmablast | Bone marrow Plasma cells |
| Single cell PCR | 38% | 66% | 71% | 50% |
| Expression & screening IgG | 36% | 66% | 71% | 50% |
| Expression & screening Ag-specific binders | 25% | 59% | 61% | 31% |

Example 1F: Affinity Measurements by SPR Using Antibody Capture Method

Positive clones expressing antigen-specific antibodies were then screened for their apparent affinity by Surface Plasmon Resonance. Anti-mouse IgG (GE Healthcare/Biacore) was coupled to the GLM by primary amine coupling. The GLM chip (BioRad) was activated using NHS/EDAC and the anti-mouse IgG coupled to this activated surface and then blocked using 1 M ethanolamine. Immobilization was carried out in either HBS-EP (Teknova) or HBS-N (GE Healthcare/Biacore) at room temperature or 37° C., respectively. The anti-mouse IgG surface on the GLM chip was used to directly capture antibodies of interest. For kinetic analysis 5 concentrations of analyte were used (256 nM, 64 nM, 16 nM, 4 nM and 1 nM). For data analysis, the binding sensorgrams were referenced using the internal "interspot" referencing unique to the ProteOn XPR36 which are double referenced using the buffer injection sensorgram. Finally the data were analyzed using the 1:1 model inherent to the ProteOn XPR36 analysis software.

Figure 9A:
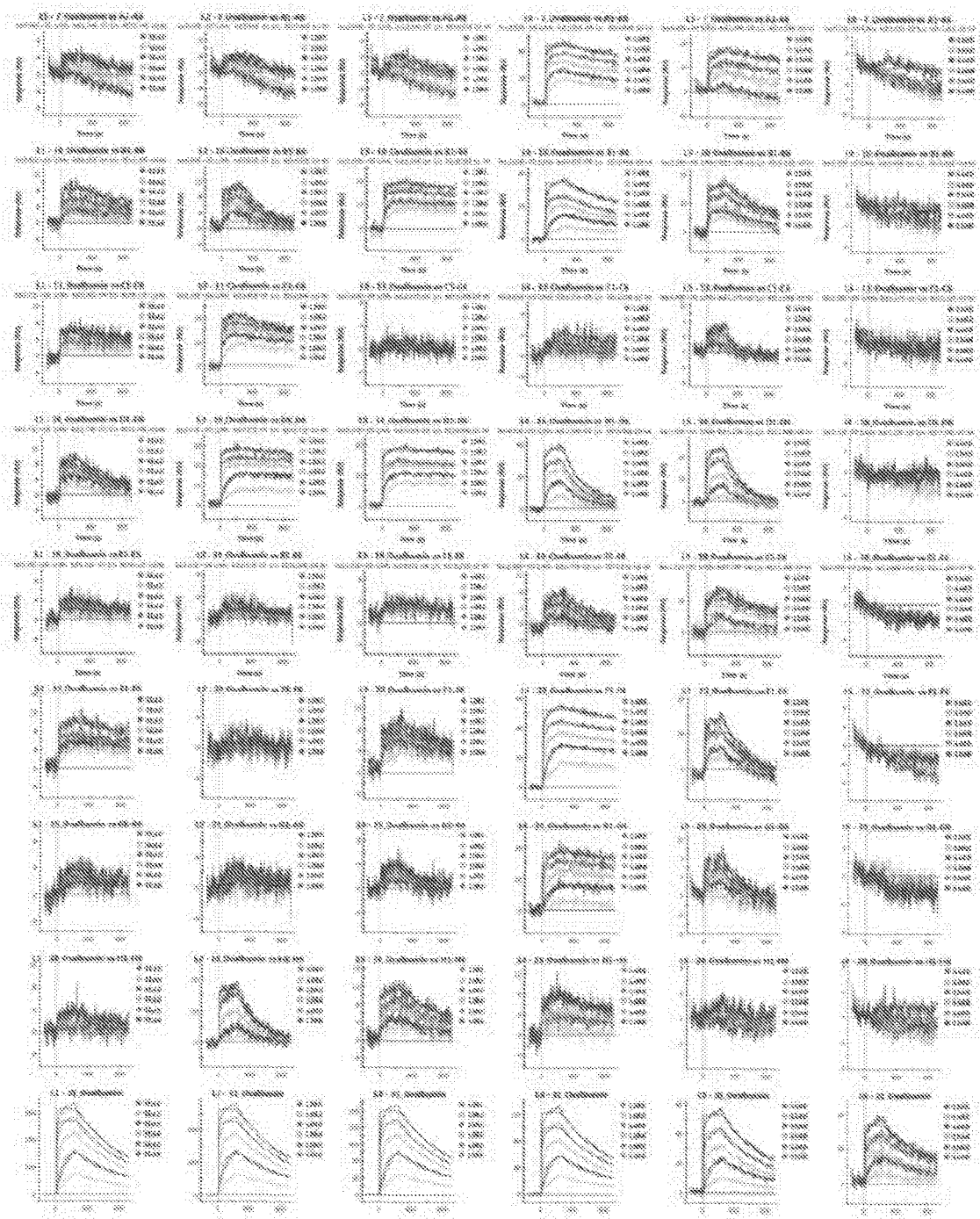
FIGS. 9A and B: Representative SPR sensorgrams of antibodies binding to ovalbumin. Around two thirds of antibodies tested showed evidence of binding to the antigen, with a diverse range of distinct binding affinities and kinetics.
Figure 9B:
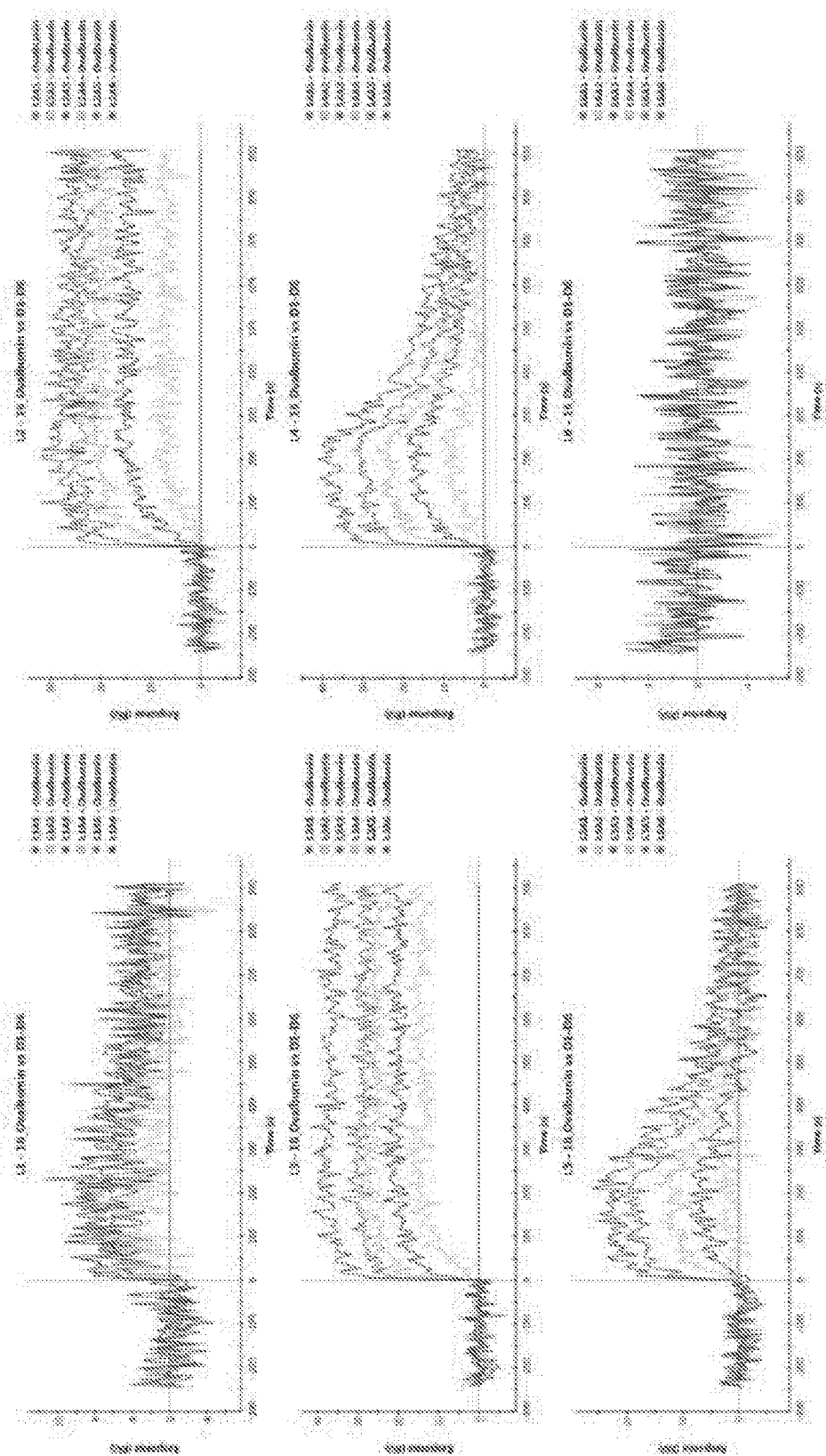

FIG. 9 is an example of SPR data of the antibodies from the ovalbumin-immunized Kymouse® using the single B cell technology of the invention. Around two thirds of antibodies tested showed evidence of binding to the antigen, with a diverse range of distinct binding affinities and kinetics. The variety of binding characteristics reveals that the cell sorting procedure is effective in capturing a diverse quality of antibodies. Despite the scale of this experiment (two animals), many high affinity antibodies in the low-nM to low-pM range were isolated verifying the efficiency of affinity maturation.

Figure 10:
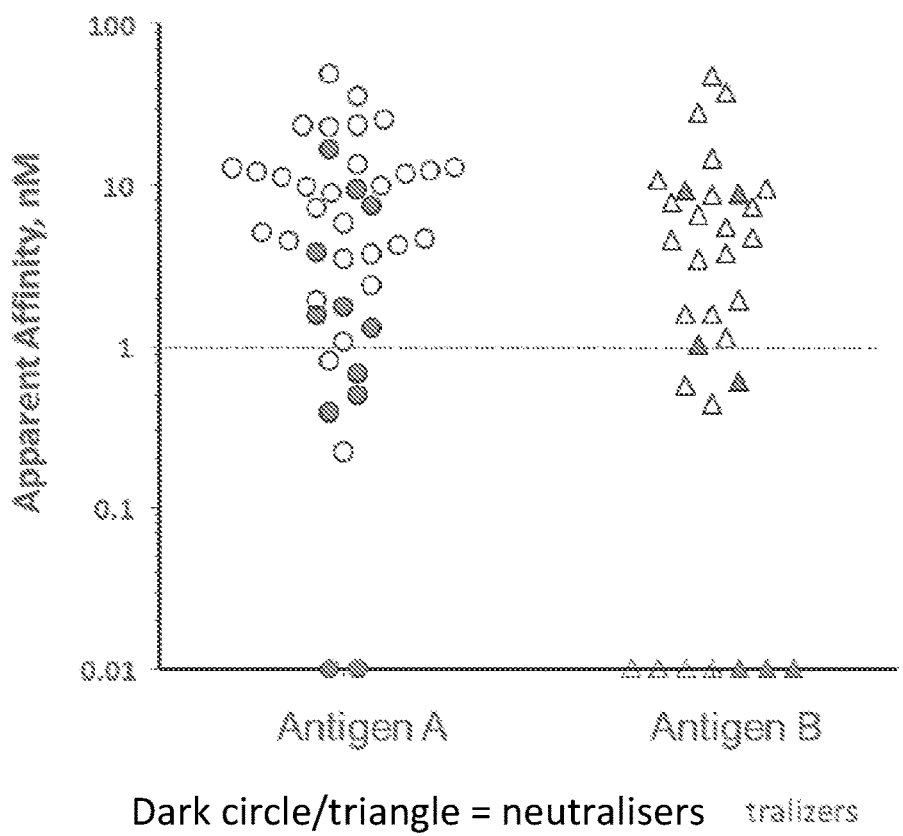
FIG. 10: The apparent affinity of antibodies against two different target antigens. A range of binders (opened) as well as functional neutralisers (filled) were detected, with the highest affinity detected in the picomolar range. This experiment validates our single B cell cloning technology to be a powerful tool in the identification and retrieval of high affinity and functionally competent antibodies.

FIG. 10 shows the apparent affinity of antibodies against two different Kymab target antigens. A range of binders (opened) as well as functional neutralisers (filled) were detected, with the highest affinity detected in the picomolar range. This validates the single B cell cloning technology of the invention to be a powerful tool in the identification and retrieval of high affinity and functionally competent antibodies.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, MA, MB, BBC, AAABCCCC, CBBAAA, CABABB, and so forth. The skilled artisan will understand that typically there is no limit on the number of items or terms in any combination, unless otherwise apparent from the context.

Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

TABLE 1

Nucleotide Sequences/Nucleic Acids:

V<sub>H</sub> Oligos

| | |
|---|---|
| SEQ ID NO: 1 | TCTAGAGAAACCCTGTGAGCACAGCTC |
| SEQ ID NO: 2 | GAGAATCCCCTGAGAGCTCCGTTC |
| SEQ ID NO: 3 | TCAGAAGCCCCCAGAGCACAACGC |
| SEQ ID NO: 4 | TGGGAGAATCCCCTAGATCACAGCTC |
| SEQ ID NO: 5 | ACAGAAGCCCCCAGAGCGCAGCAC |
| SEQ ID NO: 6 | CCCACCATGGACACACTTTGCTCC |
| SEQ ID NO: 7 | TGGACTCCAAGGCCTTTCCACTTGG |
| SEQ ID NO: 8 | TGGACCTCCTGCACAAGAACATGAAACAC |
| SEQ ID NO: 9 | GCAGTCACCAGAGCTCCAGACAATGTC |
| SEQ ID NO: 10 | AAGAAGAAGCCCCTAGACCACAGCTCCAC |
| SEQ ID NO: 11 | TGAGATTCCCAGGTGTTTCCATTCAG |
| SEQ ID NO: 12 | AGAGCCCCAGCCCCAGAATTCCCAGGAG |
| SEQ ID NO: 13 | TTCAGTGATCAGGACTGAACACACA |
| SEQ ID NO: 14 | CCCCAGCCTTGGGATTCCCAAGTGTTTTC |
| SEQ ID NO: 15 | TGAGATTCCCACGTGTTTCCATTCAG |
| SEQ ID NO: 16 | ACTTGGTGATCAGCACGGAGCACCGA |
| SEQ ID NO: 17 | CTGGGATTTTCAGGTGTTTTCATTTGG |

V<sub>K</sub> Oligos

| | |
|---|---|
| SEQ ID NO: 18 | GGAGTCAGACCCAGTCAGGACACAGC |
| SEQ ID NO: 18 | GGAGTCAGACCCACTCAGGACACAGC |
| SEQ ID NO: 20 | GGAATCAGTCCCACTCAGGACACAGC |
| SEQ ID NO: 21 | GGAGTCAGTCTCAGTCAGGACACAGC |
| SEQ ID NO: 22 | ATCAGGACTCCTCAGTTCACCTTCTCAC |
| SEQ ID NO: 23 | ATTAGGACTCCTCAGGTCACCTTCTCAC |
| SEQ ID NO: 24 | GAGGAACTGCTCAGTTAGGACCCAGA |
| SEQ ID NO: 25 | GCTACAACAGGCAGGCAGGGGCAGC |
| SEQ ID NO: 26 | GACTACCACCTGCAGGTCAGGGCCAAG |

V<sub>L</sub> Oligos

| | |
|---|---|
| SEQ ID NO: 27 | atggcctggtctcctctcctc |
| SEQ ID NO: 28 | atggccggcttccctctcctc |
| SEQ ID NO: 29 | atgccctgggctctgctcctc |
| SEQ ID NO: 30 | atgccctgggtcatgctcctc |
| SEQ ID NO: 31 | atggcctgggctctgctgctc |
| SEQ ID NO: 32 | atggcatggatccctctcttc |
| SEQ ID NO: 33 | atggcctggaccctctcctg |
| SEQ ID NO: 34 | atggcctggaccctctcctc |
| SEQ ID NO: 35 | atggcctggaccctctctgg |
| SEQ ID NO: 36 | atggcctggaccgttctcctc |
| SEQ ID NO: 37 | atggcatgggccacactcctg |
| SEQ ID NO: 38 | atggcctggatccctctactt |
| SEQ ID NO: 39 | atggcctggatccctctcctg |
| SEQ ID NO: 40 | atggcctggaccgctctcctt |
| SEQ ID NO: 41 | atggcctgggtctccttctac |
| SEQ ID NO: 42 | atggcctggaccccactcctc |
| SEQ ID NO: 43 | atggcttggaccccactcctc |
| SEQ ID NO: 44 | atggcctggactcctctcctc |
| SEQ ID NO: 45 | atggcctggactcctctctt |
| SEQ ID NO: 46 | atggcctggatgatgcttctc |
| SEQ ID NO: 47 | atggcctgggctcctctgctc |

| | Oligo | Sequence (5' to 3') |
|---|---|---|
| | \multicolumn{2}{c}{C Region Oligos} | |
| SEQ ID NO: 48 | C<sub>H</sub>1 | gctcttgcggTAGCCCTTGACCAGGCATCC |
| SEQ ID NO: 49 | C<sub>H</sub>2 | CAGATCCAGGGGCCAGTGGATAGAC |
| SEQ ID NO: 50 | C<sub>K</sub>1 | gtttctgatcgaaCTAACACTCATTCCTGTTGAAG |
| SEQ ID NO: 51 | C<sub>K</sub>2 | GACAATGGGTGAAGTTGATGTCTTGTGAG |
| SEQ ID NO: 52 | C<sub>L</sub>1 | cgacaaccactacctCTATGAACATTCTGTAGGGGC |
| SEQ ID NO: 53 | C<sub>L</sub>2 | CTTCTCCACGGTGCTCCCTTCATGC |

TABLE 2

| X | Y (i.e., sequence X used to copy or modify gene segment Y) |
|---|---|
| \multicolumn{2}{c}{V<sub>H</sub> Oligos} | |
| SEQ ID NO: 1 | IGHV1-8 (e.g., IGHV1-8*01) |
| SEQ ID NO: 2 | IGHV1-2 (e.g., IGHV1-2*04) |
| SEQ ID NO: 3 | IGHV1-3*01 (e.g., IGHV1-3*01) |
| SEQ ID NO: 4 | IGHV1-18 (e.g., IGHV1-18*01) |
| SEQ ID NO: 5 | IGHV1-24 (e.g., IGHV1-24*01) |
| SEQ ID NO: 6 | IGHV2-5 (e.g., IGHV2-5*10) and/or IGHV2-26 (e.g., IGHV2-26*01) |
| SEQ ID NO: 7 | IGHV3-7 (e.g., IGHV3-7*01) |
| SEQ ID NO: 8 | IGHV4-4 (e.g., IGHV4-4*02) |
| SEQ ID NO: 9 | IGHV6-1 (e.g., IGHV6-1*01) |
| SEQ ID NO: 10 | IGHV7-4-1 (e.g., IGHV7-4-1*01) |
| SEQ ID NO: 11 | IGHV3-9 (e.g., IGHV3-9*01) |
| SEQ ID NO: 12 | IGHV3-11 (e.g., IGHV3-11*01) |
| SEQ ID NO: 13 | IGHV3-13 (e.g., IGHV3-13*01) |
| SEQ ID NO: 14 | IGHV3-15 (e.g., IGHV3-15*01) |
| SEQ ID NO: 15 | IGHV3-20 (e.g., IGHV3-20*01) |
| SEQ ID NO: 16 | IGHV3-21 (e.g., IGHV3-21*01) |
| SEQ ID NO: 17 | IGHV3-23 (e.g., IGHV3-23*01) |
| \multicolumn{2}{c}{VK Oligos} | |
| SEQ ID NO: 18 | One, more or all of IGKV1-5, 1-12, 1-8, 1D-8, 1D-43, 1D-16, 1D-9 |
| SEQ ID NO: 19 | One, more or all of IGKV1-6, 1-13, 1D-12, 1D-13 |

TABLE 2-continued

| X | Y (i.e., sequence X used to copy or modify gene segment Y) |
|---|---|
| SEQ ID NO: 20 | IGKV1-17 and/or 1D-17 |
| SEQ ID NO: 21 | One, more or all of IGKV1-27, 1-33, 1D-39 |
| SEQ ID NO: 22 | One, more or all of IGKV2-28, 2-30, 2D-40 |
| SEQ ID NO: 23 | IgKV2-24 |
| SEQ ID NO: 24 | IGKV3 Family |
| SEQ ID NO: 25 | IGKV4-1 |
| SEQ ID NO: 26 | IGKV5-2 |
| VL Oligos | |
| SEQ ID NO: 27 | IGLV1-40 |
| SEQ ID NO: 28 | IGLV1-47 |
| SEQ ID NO: 29 | IGLV10-54 |
| SEQ ID NO: 30 | IGLV2-23 |
| SEQ ID NO: 31 | IGLV3-1 |
| SEQ ID NO: 32 | IGLV3-10 |
| SEQ ID NO: 33 | IGLV3-12 |
| SEQ ID NO: 34 | IGLV3-19 |
| SEQ ID NO: 35 | IGLV3-21 |
| SEQ ID NO: 36 | IGLV3-22 |
| SEQ ID NO: 37 | IGLV3-25 |
| SEQ ID NO: 38 | IGLV3-16 |
| SEQ ID NO: 39 | IGLV3-9 |
| SEQ ID NO: 40 | IGLV4-3 |
| SEQ ID NO: 41 | IGLV3-2 |
| SEQ ID NO: 42 | IGLV5-45 |
| SEQ ID NO: 43 | IGLV7-43 |
| SEQ ID NO: 44 | IGLV9-49 |
| SEQ ID NO: 45 | IGLV1-40 |
| SEQ ID NO: 46 | IGLV1-47 |
| SEQ ID NO: 47 | IGLV10-54 |

What is claimed is:

1. A method of producing cells encoding a repertoire of antibody binding sites comprising a VH sequence and VL sequence, the method comprising:
   a) providing a population of cells expressing a repertoire of antibody binding sites, which cells are isolated from one or more animals and which comprise B cells, germinal center cells, memory B cells, antibody-secreting cells, plasma cells, or plasmablast cells;
   b) sorting the population of cells by binding the antibody binding sites to an antigen of interest to produce a sorted population of single cells, each cell comprising nucleic acid encoding a respective antibody binding site, and each sorted cell provided in a separate container;
   c) amplifying the nucleic acid comprised by the sorted single cell population using PCR to produce a sorted repertoire of amplified nucleic acids encoding antibody binding sites, wherein the VH and VL sequences of each antibody binding site are amplified in the same container;
   d) modifying the sorted amplified antibody binding site-encoding nucleic acids from step (c) to produce a sorted repertoire of expression cassettes, each container comprising a first type of cassette comprising a nucleotide sequence encoding a VH sequence of an antibody binding site and one or more regulatory elements for expressing the VH sequence of the antibody binding site from said single cell, and a second type of cassette comprising a nucleotide sequence encoding a VL sequence of an antibody binding site and one or more regulatory elements for expressing the VL sequence of the antibody binding site from said single cell, wherein the VH and VL sequences of each antibody binding site are modified in the same container; and
   e) transferring the antibody binding site expression cassettes from said cassette repertoire to a sorted population of host cells while maintaining the antibody binding site expression cassette sorting and producing a sorted repertoire of host cells that expresses a sorted repertoire of antibody binding sites, wherein the sorted repertoire of host cells is capable of stably expressing the repertoire of antibody binding sites.

2. The method of claim 1, wherein in step (e) the sorted expression cassettes are batch transferred to the sorted host cells.

3. The method of claim 2, wherein in step (e) the sorted expression cassettes are transferred without purification.

4. The method of claim 1, wherein (i) the sorted repertoire of expression cassettes produced by step (d) is provided in a plurality of containers whose locations relative to each other are fixed, wherein each container comprises a respective type of expression cassette such that the relative location of expression cassettes relative to each other is predetermined; and (ii) the expression cassettes are transferred to the sorted host cells in step (e) such that the relative locations of the expression cassettes is maintained.

5. The method of claim 1, further comprising:
   screening the sorted antibody binding site repertoire to identify a antibody binding site with a desired characteristic and/or the nucleotide sequence encoding the identified antibody binding site;
   identifying, amplifying or synthesizing the nucleotide sequence encoding the identified antibody binding site; and producing isolated antibody binding site using said identified, amplified or synthesized nucleotide sequence.

6. The method of claim 1, further comprising:
   screening the sorted antibody binding site repertoire to identify a antibody binding site with a desired characteristic and isolating a host cell expressing the identified antibody binding site;
   and propagating the cell to produce a cell line expressing the antibody binding site.

7. The method of claim 1, wherein step (e) comprises genomically-integrating antibody binding site expression cassettes into respective host cell genomes for expressing the respective antibody binding sites, wherein said genomic integration is carried out using a predetermined genomic nucleotide sequence motif for insertion of the expression cassettes into the respective cell genome.

8. The method of claim 7, wherein said genomic integration is carried out by transposon-mediated integration.

9. The method of claim 1, wherein the antigen is a fluorescently-labelled antigen; or a virus-like particle (VLP) comprising an expressed antigen on the surface and further comprising a fluorescently labelled protein.

10. The method of claim 1, wherein the population of cells in step (a) is further identified by the presence of one or more cell surface markers selected from the group consisting of: CD19, IgM, IgD, CD38, and CD95.

11. The method of claim 1, wherein
   (i) the repertoire of expression cassettes produced by step (d) is sorted by providing a plurality of containers, wherein each container comprises antibody binding site-encoding sequences of a single cell sorted in step (b);
   (ii) the sorted host cells of step (e) are provided in a plurality of containers; and
   (iii) the expression cassettes are transferred to the sorted host cells in step (e) such that host cells in each respective container are mixed only with antibody binding site-encoding sequences derived from a single cell sorted in step (b).

12. The method of claim 1, wherein, in step (b), FACS or fluorescence FACS cell sorting is used.

13. The method of claim 1, wherein step (d) comprises modification of the amplified nucleic acids by combination with a predetermined sequence so that said predetermined sequence flanks 5' and/or 3' of the antibody binding site-encoding nucleotide sequences of the nucleic acids; wherein the modification places a regulatory element and a transposon element flanking 5' and/or 3' of the antibody binding site-encoding nucleotide sequences.

14. The method of claim 1, wherein in step (d) modification is carried out using bridge PCR to produce a repertoire of expression cassettes comprising 5'- and 3'-terminal transposon elements with an antibody binding site-encoding nucleotide sequence and one or more regulatory elements for antibody binding site expression between the transposon elements.

15. The method of claim 1, wherein the host cell is a eukaryotic cell.

16. The method of claim 1, wherein one or more the expression cassettes of step (d) are configured to express the antibody binding sites in combination with a constant region of an antibody chain.

* * * * *